US012605463B2

(12) United States Patent
Green et al.

(10) Patent No.: US 12,605,463 B2
(45) **Date of Patent: *Apr. 21, 2026**

(54) TOLEROGENIC ARTIFICIAL ANTIGEN-PRESENTING CELLS

(71) Applicant: The Johns Hopkins University, Baltimore, MD (US)

(72) Inventors: Jordan J. Green, Baltimore, MD (US); Kelly Rhodes, Baltimore, MD (US); Randall A. Meyer, Baltimore, MD (US); Stephany Yi Tzeng, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/602,932

(22) PCT Filed: Jun. 12, 2020

(86) PCT No.: PCT/US2020/037424

§ 371 (c)(1),
(2) Date: Oct. 11, 2021

(87) PCT Pub. No.: WO2020/210843

PCT Pub. Date: Oct. 15, 2020

(65) Prior Publication Data

US 2022/0249696 A1 Aug. 11, 2022

Related U.S. Application Data

(60) Provisional application No. 62/832,957, filed on Apr. 12, 2019.

(51) Int. Cl.

| | |
|---|---|
| ***A61K 47/69*** | (2017.01) |
| ***A61K 31/436*** | (2006.01) |
| ***A61K 31/496*** | (2006.01) |
| ***A61K 38/18*** | (2006.01) |
| ***A61K 39/00*** | (2006.01) |
| ***A61K 47/64*** | (2017.01) |
| ***A61K 47/68*** | (2017.01) |
| ***A61P 37/06*** | (2006.01) |

(52) U.S. Cl.

CPC ........ *A61K 47/6937* (2017.08); *A61K 31/436* (2013.01); *A61K 38/1841* (2013.01); *A61K 39/0008* (2013.01); *A61K 47/6425* (2017.08); *A61K 47/646* (2017.08); *A61K 47/6849* (2017.08); *A61P 37/06* (2018.01)

(58) Field of Classification Search

CPC ............ A61K 47/6937; A61K 47/6425; A61K 47/646; A61K 47/6849; A61K 31/436; A61K 38/1841; A61K 39/0008; A61P 37/06

See application file for complete search history.

(56) References Cited

U.S. PATENT DOCUMENTS

| | | | | |
|---|---|---|---|---|
| 6,787,154 | B2 | 9/2004 | Albani | |
| 7,943,179 | B2 * | 5/2011 | Little | A61K 9/1647 424/490 |
| 8,992,991 | B2 | 3/2015 | Green et al. | |
| 9,717,694 | B2 | 8/2017 | Green et al. | |
| 9,802,984 | B2 | 10/2017 | Popel et al. | |
| 9,884,118 | B2 | 2/2018 | Green et al. | |
| 2002/0131960 | A1 | 9/2002 | Sadelain et al. | |
| 2010/0028450 | A1 | 2/2010 | Vasu | |
| 2010/0047262 | A1 | 2/2010 | Rasmussen et al. | |
| 2010/0196492 | A1 * | 8/2010 | Green | A61P 29/00 514/23 |
| 2010/0233079 | A1 | 9/2010 | Jakob et al. | |
| 2012/0114759 | A1 | 5/2012 | Green et al. | |
| 2013/0052212 | A1 | 2/2013 | Har-Noy | |
| 2014/0370099 | A1 | 12/2014 | Green et al. | |
| 2015/0273071 | A1 | 10/2015 | Green et al. | |
| 2016/0045551 | A1 | 2/2016 | Brentjens et al. | |
| 2017/0114130 | A1 | 4/2017 | Rondon et al. | |
| 2017/0216363 | A1 | 8/2017 | Quinones-Hinojosa et al. | |
| 2018/0112038 | A1 | 4/2018 | Green et al. | |
| 2018/0221337 | A1 | 8/2018 | Slusher et al. | |
| 2018/0256745 | A1 | 9/2018 | Meyer et al. | |
| 2018/0346969 | A1 | 12/2018 | Chang et al. | |
| 2018/0369333 | A1 * | 12/2018 | Fahmy | A61K 9/1271 |

OTHER PUBLICATIONS

R. A. Meyer, J. C. Sunshine, and J. J. Green. "Biomimetic particles as therapeutics," Trends in Biotechnology, Sep. 2015, vol. 33, No. 9, 514-524). (Year: 2015).*
International Search Report and Written Opinion for PCT/US20/37424. Mailed Oct. 14, 2020. 15 pages.
Avidin. Wikipedia Nov. 7, 2018. Retreived Aug. 30, 2020. 3 pages.
Biotin anti-mouse antibody. Nov. 20, 2012. Retreived from internet Aug. 30, 2020. 3 pages.
Champion et al., Role of target geometry in phagocytosis. Proc Natl Acad Sci U S A. Mar. 28, 2006;103(13):4930-4.
Chen et al., Conversion of peripheral CD4+CD25-naive T cells to CD4+CD25+ regulatory T cells by TGF-beta induction of transcription factor Foxp3. J Exp Med. Dec. 15, 2003;198(12):1875-86.

(Continued)

*Primary Examiner* — Michael P Cohen
(74) *Attorney, Agent, or Firm* — Casimir Jones, SC; Jeffrey W. Childers

(57) ABSTRACT

Biodegradable particles for interacting with immune cells to generate an immunosuppressive effect are disclosed. The biodegradable particle comprises a polyester or polyester blend with at least one soluble protein or small molecule encapsulated within the particle and at least two types of protein attached to a surface of the particle or to a coating on the surface thereof, which can be used to induce targeting regulatory T cells (Tregs). The at least two types of protein attached to a surface of the particle or to a coating on the surface thereof include a "Signal 1" protein that binds to an immune cell and a "Signal 2" protein that acts as a co-stimulatory molecule to immune cells. The encapsulated protein can be an interleukin and/or a cytokine. Methods of their use for treating a disease or condition, including an autoimmune disease, are disclosed.

23 Claims, 25 Drawing Sheets
(22 of 25 Drawing Sheet(s) Filed in Color)

(56) References Cited

OTHER PUBLICATIONS

Cheung et al., Scaffolds that mimic antigen-presenting cells enable ex vivo expansion of primary T cells. Nat Biotechnol. Feb. 2018;36(2):160-169.
Gliwinski et al., Cell-Based Therapies with T Regulatory Cells. BioDrugs. Aug. 2017;31(4):335-347.
Hsu et al., Ligand mobility modulates immunological synapse formation and T cell activation. PLoS One. 2012;7(2):e32398. 10 pages.
Li et al., Suppression of ongoing T cell-mediated autoimmunity by peptide-MHC class II dimer vaccination. J Immunol. Oct. 1, 2009;183(7):4809-16.
Lin et al., Reversal of type 1 diabetes by a new MHC II-peptide chimera: "Single-epitope-mediated suppression" to stabilize a polyclonal autoimmune T-cell process. Eur J Immunol. Aug. 2010;40(8):2277-88.
Little et al., Poly-beta amino ester-containing microparticles enhance the activity of nonviral genetic vaccines. Proc Natl Acad Sci USA. Jun. 29, 2004;101(26):9534-9.
Long et al., CD4+FOXP3+ T regulatory cells in human autoimmunity: more than a numbers game. J Immunol. Sep. 1, 2011;187(5):2061-6.
Matic et al., Fine tuning and efficient T cell activation with stimulatory aCD3 nanoarrays. Nano Lett. Nov. 13, 2013;13(11):5090-7.
McHugh et al., Paracrine co-delivery of TGF-β and IL-2 using CD4-targeted nanoparticles for induction and maintenance of regulatory T cells. Biomaterials. Aug. 2015;59:172-81.
O'Connor et al., Substrate rigidity regulates human T cell activation and proliferation. J Immunol. Aug. 1, 2012;189(3):1330-9.
Sabatos-Peyton et al., Antigen-specific immunotherapy of autoimmune and allergic diseases. Curr Opin Immunol. Oct. 2010;22(5):609-15.
Sakaguchi et al., Immunologic self-tolerance maintained by activated T cells expressing IL-2 receptor alpha-chains (CD25). Breakdown of a single mechanism of self-tolerance causes various autoimmune diseases. J Immunol. Aug. 1, 1995;155(3):1151-64.
Sarkar et al., Ex Vivo Expanded Autologous Polyclonal Regulatory T Cells Suppress Inhibitor Formation in Hemophilia. Mol Ther Methods Clin Dev. Jul. 30, 2014;1:14030.
Steenblock et al., An artificial antigen-presenting cell with paracrine delivery of IL-2 impacts the magnitude and direction of the T cell response. J Biol Chem. Oct. 7, 2011;286(40):34883-92.
Sunshine et al., Particle shape dependence of CD8+ T cell activation by artificial antigen presenting cells. Biomaterials. Jan. 2014;35(1):269-277.
Tang et al., In vitro-expanded antigen-specific regulatory T cells suppress autoimmune diabetes. J Exp Med. Jun. 7, 2004;199(11):1455-65.
Tzeng et al., Non-viral gene delivery nanoparticles based on poly(β-amino esters) for treatment of glioblastoma. Biomaterials. Aug. 2011;32(23):5402-10.
Vignali et al., How regulatory T cells work. Nat Rev Immunol. Jul. 2008;8(7):523-32.
Webster et al., In vivo expansion of T reg cells with IL-2-mAb complexes: induction of resistance to EAE and long-term acceptance of islet allografts without immunosuppression. J Exp Med. Apr. 13, 2009;206(4):751-60.
Yamazaki et al., Direct expansion of functional CD25+ CD4+ regulatory T cells by antigen-processing dendritic cells. J Exp Med. Jul. 21, 2003;198(2):235-47.
Zhang et al., Paracrine release of IL-2 and anti-CTLA-4 enhances the ability of artificial polymer antigen-presenting cells to expand antigen-specific T cells and inhibit tumor growth in a mouse model. Cancer Immunol Immunother. Sep. 2017;66(9):1229-1241.
Eggermont et al., Towards efficient cancer immunotherapy: advances in developing artificial antigen-presenting cells. Trends Biotechnol. Sep. 2014;32(9):456-65.
Hasan et al., Artificial Antigen Presenting Cells: An Off the Shelf Approach for Generation of Desirable T-Cell Populations for Broad Application of Adoptive Immunotherapy. Adv Genet Eng. 2015;4(3):130.Epub Oct. 5, 2015.
Tan et al., Creation of Tolerogenic Antigen Presenting Cells Via Intracellular CTLA4: A Novel Strategy With Potential Clinical Utility In Transplantation. Transplantation., 2004, vol. 78(2), pp. 517-518.
Wan et al., A Tolerogenic Artificial APC Durably Ameliorates Experimental Autoimmune Encephalomyelitis by Directly and Selectively Modulating Myelin Peptide-Autoreactive CD4 + and CD8 T Cells. J Immunol. Aug. 15, 2018;201(4):1194-1210.
A. Salerno, et al. The effect of cyclosporin A, FKS06 and rapamycin on the murine contact sensitivity reaction. Clin. Exp. Immunol. 1998; 112: 112-119. (Year: 1998).
Battaglia M., et al., "Immune Intervention With T Regulatory Cells: Past Lessons and Future Perspectives for Type 1 Diabetes," Seminars in Immunology, 2011, vol. 23, No. 3, pp. 182-194.
Ben-Akiva E., et al., "Polymeric Micro-and Nanoparticles for Immune Modulation," Biomaterials Science, Nov. 1, 2018, vol. 7, No. 1, pp. 14-30.
Bluestone J.A., et al., "T Reg Cells-the Next Frontier of Cell Therapy," Science, Oct. 12, 2018, vol. 362, No. 6411, pp. 154-155 (3 Pages).
Boder E.T., et al., "Yeast Surface Display for Screening Combinatorial Polypeptide Libraries," Nature Biotechnology, Jun. 1997, vol. 15, No. 6, pp. 553-557.
Boyman O., et al., "Selective Stimulation of T Cell Subsets With Antibody-Cytokine Immune Complexes," Science, Mar. 31, 2006, vol. 311, No. 5769, pp. 1924-1927 (5 Pages).
Boyman O., et al., "The Role of Interleukin-2 During Homeostasis and Activation of the Immune System," Nature Reviews Immunology, Mar. 2012, vol. 12, No. 3, pp. 180-190.
Bromberg J., et al., "Inflammation and Cancer: IL-6 and STAT3 Complete the Link," Cancer Cell, Feb. 3, 2009, vol. 15, No. 2, pp. 79-80.
Buckner., Mechanisms of impaired regulation by CD4(+)CD25(+)FOXP3(+) regulatory T cells in humanautoimmune diseases., Nature Reviews Immunology., (2010), pp. 849-859, vol. 10(12).
Clemente-Casares et aL, Expanding antigen-specific regulatory networks to treat autoimmunity., Nature.,(2016), pp. 434-440, vol. 530(7591).
Crawford F., et al., "Specificity and Detection of Insulin-Reactive CD4+ T Cells in Type 1 Diabetes in the Nonobese Diabetic (NOD) Mouse," Proceedings of the National Academy of Sciences of the United States of America, Oct. 4, 2011, vol. 108, No. 40, pp. 16729-16734.
Dawson N.A.J., et al., "Engineered Tolerance: Tailoring Development, Function, and Antigen-Specificity of Regulatory T Cells," Frontiers in Immunology, Nov. 2017, vol. 8, Article 1460, 8 Pages.
Elessawy B., et al., "Type 1 Diabetes and T Regulatory Cells," Pharmacology Research, 2015, vol. 98, pp. 22-30.
Extended European Search Report for European Application No. 20801487.8, mailed Apr. 6, 2023, 13 Pages.
Grinberg-Bleyer Y., et al., "IL-2 Reverses Established Type 1 Diabetes in NOD Mice by a Local Effect on Pancreatic Regulatory T Cells," The Journal of Experimental Medicine, Aug. 30, 2010, vol. 207, No. 9, pp. 1871-1878, (Aug. 2, 2010).
Horwitz D.A., et al., "Suppression of Murine Lupus by CD4+ and CD8+ Treg Cells Induced By T Cell-Targeted Nanoparticles Loaded With Interleukin-2 and Transforming Growth Factor Beta," Arthritis & Rheumatology, Apr. 2019, vol. 71, No. 4, pp. 632-640, EPublished Mar. 5, 2019.
International Search Report and Written Opinion for International Application No. PCT/US2020/027989, mailed Nov. 18, 2020, 9 Pages.
Jhunjhunwala S., et al., "Delivery of Rapamycin to Dendritic Cells Using Degradable Microparticles," Journal of Control Release, 2009, vol. 133, No. 3, pp. 191-197.
Klatzmann D., et al., "The Promise of Low-dose Interleukin-2 Therapy for Autoimmune and Inflammatory Diseases," Nature Reviews Immunology, May 2015, vol. 15, No. 5, pp. 283-294.
Kuziel W.A., et al., "Unexpected Effects of the IL-2 Receptor Alpha Subunit on High Affinity IL-2 Receptor Assembly and Function

(56) References Cited

OTHER PUBLICATIONS

Detected With a Mutant IL-2 Analog," Journal of Immunology, 1993, vol. 150, No. 8, pp. 3357-3365 (10 pages).
Lee K., et al., "Attenuation of Donor-Reactive T Cells Allows Effective Control of Allograft Rejection Using Regulatory T Cell Therapy," American Journal of Transplantation, 2014, vol. 14, No. 1, pp. 27-38.
Liao W., et al., "Interleukin-2 at the Crossroads of Effector Responses, Tolerance, and Immunotherapy," Immunity, Jan. 24, 2013, vol. 38, No. 1, pp. 13-25.
Liu R., et al., "Expansion of Regulatory T Cells via IL-2/anti-IL-2 mAb Complexes Suppresses Experimental Myasthenia," European Journal of Immunology, 2010, vol. 40, No. 6, pp. 1577-1589.
Maahs D.M., et al., "Mortality and Renal Disease in Type 1 Diabetes Mellitus- Progress Made, more to Be Done," The Journal of Clinical Endocrinology & Metabolism, Oct. 2010, vol. 91, No. 10, pp. 3757-3759.
Malek T.R., "The Biology of Lnterleukin-2," Annual Review of Immunology, 2008, vol. 26, No. 1, pp. 453-479 (29 Pages).
Marek-Trzonkowska N., et al., "Administration of Cd4+ CD25highCD127—Regulatory T Cells Preserves Beta-Cell Function in Type 1 Diabetes in Children," Diabetes Care, Sep. 2012, vol. 35, No. 9, pp. 1817-1820.
Meyer R.A., et al., "Biodegradable Nanoellipsoidal Artificial Antigen Presenting Cells for Antigen Specific T-Cell Activation," Small, 2015, vol. 11, No. 13, pp. 1519.1525.
Murray., The JAK-STAT signaling pathway: input and output integration., Journal of Immunology., (2007), pp. 2623-2629, vol. 178(5).
Oelke et aL, Ex vivo induction and expansion of antigen-specific cytotoxic T cells by HLA-Ig-coated artificial antigen-presenting cells., Nature Medicine., (2003), pp. 619-624, vol. 9(5).
Pasche N., et al., "Immunocytokines: A Novel Class of Potent Armed Antibodies," Drug Discovery Today, Jun. 2012, vol. 17, No. 111/12, pp. 583-590.
Patterson C., et al., "Diabetes in the Young—A Global View and Worldwide Estimates of Numbers of Children With Type 1 Diabetes," Diabetes Research and Clinical Practice, 2014, vol. 103, No. 2, pp. 161-175.
Pei W., et al., "Direct Modulation of Myelin-autoreactive CD4+ and CD8+ T Cells in EAE Mice by a Tolerogenic Nanoparticle Co-Carrying Myelin Peptide-Loaded Major Histocompatibility Complexes, CD47 and Multiple Regulatory Molecules," International Journal of Nanomedicine, vol. 13, Jun. 27, 2018, pp. 3731-3750.
Raimondi G., et al., "Ammalian Target of Rapamycin Inhibition and Alloantigen-Specific Regulatory T Cells Synergize to Promote Long-term Graft Survival in Immunocompetent Recipients," Journal of Immunology, 2010, vol. 184, No. 2, pp. 624-636 (14 Pages).
Ring A.M., et al., "Mechanistic and Structural Insight Into the Functional Dichotomy Between IL-2 and IL-15," Nature Immunology, Dec. 2012, vol. 13, No. 12, pp. 1187-1195 (11 Pages).
Roncarolo M-G., et al., "Regulatory T-Cell Immunotherapy for Tolerance to Self Antigens and Alloantigens in Humans," Nature Reviews Immunology, Aug. 2007, vol. 7, No. 8, pp. 585-598.
Rossjohn J., et al., "T Cell Antigen Receptor Recognition of Antigen-Presenting Molecules," Annual Review of Immunology, 2015, vol. 33, No. 1, pp. 169-200 (34 Pages).
Spangler J.B., et al., "Antibodies to Interleukin-2 Elicit Selective T Cell Subset Potentiation through Distinct Conformational Mechanisms," Immunity, May 19, 2015, vol. 42, No. 5, pp. 815-825 (12 Pages).
Spangler J.B., et al., "Engineering a Single-Agent Cytokine/Antibody Fusion That Selectively Expands Regulatory T Cells for Autoimmune Disease Therapy," Journal of Immunology, 2018, vol. 201, No. 7, pp. 2094-2106 (14 Pages).
Steffes M.W., et al., "Sustained Effect of Intensive Treatment of Type 1 Diabetes Mellitus on Development and Progression of Diabetic Nephropathy: The Epidemiology of Diabetes Interventions and Complications (EDIC) Study," JAMA, Writing Team for the Diabetes Control and Complications Trial/epidemiology of Diabetes Interventions and Complications Research Group, Oct. 22, 2003, vol. 290, No. 16, pp. 2159-2167 (17 Pages).
Tang et aL, Central role of defective interleukin-2 production in the triggering of islet autoimmune destruction., Immunity., (2008), pp. 687-697, vol. 28(5).
Tang Q., et al., "Transplant Trials With Tregs: Perils and Promises," Journal of Clinical Investigation, Jul. 2017, vol. 127, No. 7, pp. 2505-2512 (9 Pages).
Trotta E., et al., "A Human Anti-il-2 Antibody That Potentiates Regulatory T Cells by a Structure-based Mechanism," Nature Medicine, Jul. 2018, vol. 24, No. 7, pp. 1005-1014 (17 Pages).
Turnquist H.R., et al., "Rapamycin-Conditioned Dendritic Cells Are Poor Stimulators of Allogeneic CD4+ T Cells, but Enrich for Antigen-Specific Foxp3+ T Regulatory Cells and Promote Organ Transplant Tolerance," Journal of Immunology, 2007, vol. 178, No. 11, pp. 7018-7031.
Ugel et aL, In vivo Administration of Artificial Antigen-Presenting Cells Activates Low-Avidity T Cells for Treatment of Cancer., Cancer Research., (2009), pp. 9376-9384, vol. 69(24).
Walker L.S.K., "Regulatory T Cells Overturned: the Effectors Fight Back," Immunology, 2009, vol. 126, No. 4, pp. 466-474.
Wang X., et al., "Structure of the Quaternary Complex of Interleukin-2 With Its Alpha, Beta, and Gammac Receptors," Science, Nov. 18, 2005, vol. 310, No. 5751, pp. 1159-1163 (6 Pages).
Wesley J.D., et al., "Cellular Requirements for Diabetes Induction in DO11.10xRIPmOVA Mice.," Journal of Immunology, 2010, vol. 185, No. 8, pp. 4760-4768.
Yodoi J., et al., "TCGF (IL 2))-Receptor Inducing Factor(S). I. Regulation of Il 2 Receptor on a Natural Killer-Like Cell Line(YT Cells)," Mar. 1985, vol. 134, No. 3, pp. 1623-1630.
You W-P., et al., "Type 1 Diabetes Prevalence Increasing Globally and Regionally: The Role of Natural Selection and Life Expectancy at Birth," BMJ Open Diabetes Research & Care, 2016, vol. 4, No. 1, e000161, 7 Pages.

* cited by examiner 1,4 Butanediol diacrylate (B4)

4,4'-Trimethylenedipiperidine (Sp)

Acrylate-terminated poly(β-amino ester)

1-(3-Aminopropyl)-4-methylpiperazine (E7)

Endcapped poly(β-amino ester)

Fig. 8B
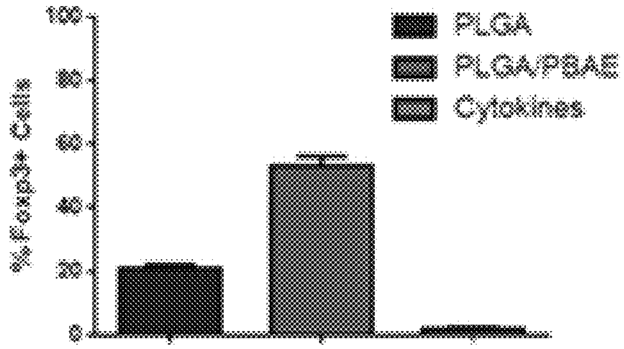
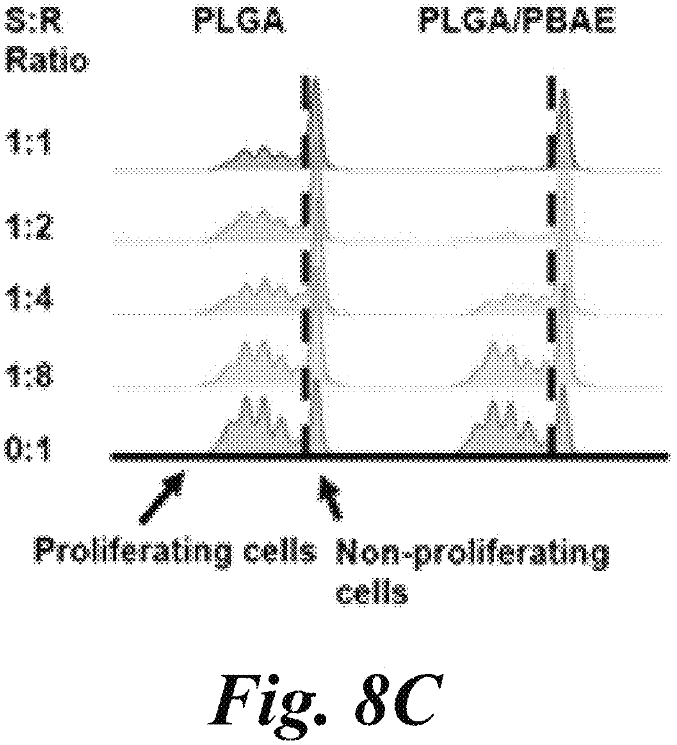
Fig. 8C

*Fig. 9B*
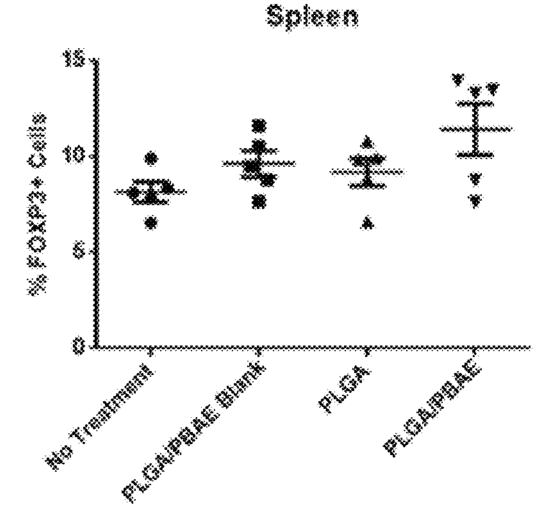
*Fig. 9C*
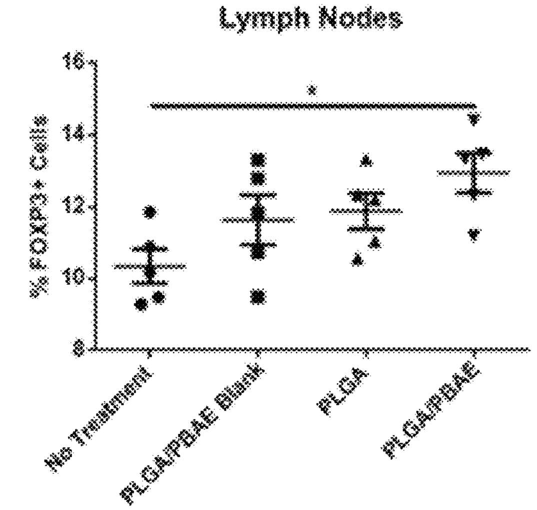
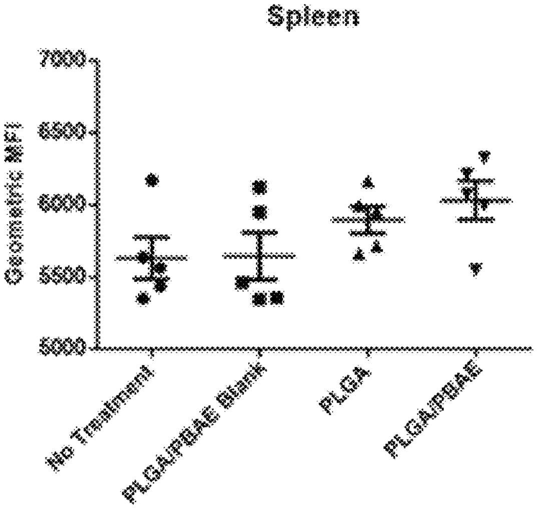
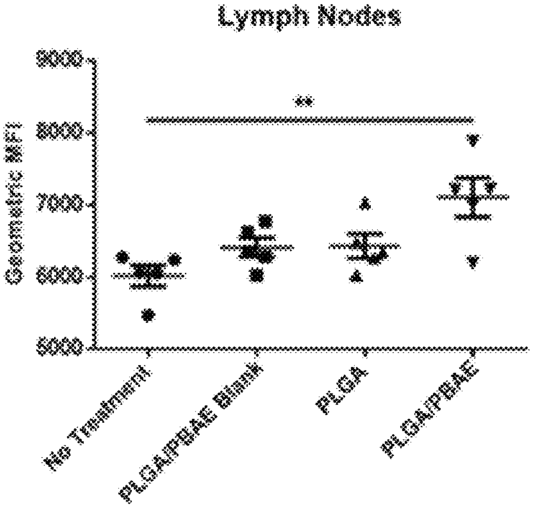
*Fig. 9D*
*Fig. 9E*

TOLEROGENIC ARTIFICIAL ANTIGEN-PRESENTING CELLS

FEDERALLY SPONSORED RESEARCH OR DEVELOPMENT

This invention was made with government support under EB022148 awarded by the National Institutes of Health and DGE1232825 awarded by the National Science Foundation. The government has certain rights in the invention.

BACKGROUND

Autoimmune diseases are often treated with immunosuppressants that weaken the entire immune system, leaving patients vulnerable to infection. An ideal autoimmune therapy establishes immune tolerance to the specific self-antigen(s) recognized by the host immune system, while the rest of the immune system remains intact. See Sabatos-Peyton C. et al. *Curr. Opin. Immunol.* 2010. One strategy for establishing antigen-specific immune tolerance is targeting regulatory T cells (Tregs), which maintain immune homeostasis and dampen immune responses to self-antigens through a variety of mechanisms and are fundamental controllers of the destructive arm of the immune system. Vignali D, et al. *Nat Rev Immunol.* 2008.

SUMMARY

In some aspects, the presently disclosed subject matter provides a biodegradable particle comprising a polyester or polyester blend with at least one soluble protein or small molecule encapsulated within the particle and at least two types of protein attached to a surface of the particle or to a coating on the surface thereof. In particular aspects, the polyester blend is a blend of poly(lactic-co-glycolic acid) (PLGA) and poly(beta-amino ester) (PBAE). In certain aspects, these biodegradable particles induce the stimulation and/or expansion of regulatory T cells.

In other aspects, the at least two types of protein attached to a surface of the particle or to a coating on the surface thereof include a "Signal 1" protein that binds to an immune cell and a "Signal 2" protein that acts as a co-stimulatory molecule to immune cells. In particular aspects, the immune cell to which the Signal 1 protein binds comprises a T cell. In certain aspects, the Signal 1 protein is selected from the group consisting of an anti-CD3 monoclonal antibody, major histocompatibility complex (MHC)-peptide complex (including human leukocyte antigen (HLA) complex), and one or more T-cell receptor (TCR) binders. In other aspects, the Signal 2 protein is selected from the group consisting of anti-CD28, 4-1BBL, CD80, CD86, and OX40L.

In yet other aspects, the at least one soluble protein encapsulated within the particle comprises a "Signal 3" protein, including an interleukin and/or a cytokine, such as transforming growth factor beta 1 (TGF-β1).

In some aspects, the particle is microparticle having an average diameter of from about 1 micron to about 5 microns. In other aspects, the particle is a nanoparticle having an average diameter of from about 50 nm to about 1000 nm. In certain aspects, the particle is anisotropic and has a non-spherical shape. In particular aspects, the particle has a prolate ellipsoidal shape.

In other aspects, the particle has a coating comprising one or more synthetic and/or natural lipids and/or lipid membranes. In such aspects, the at least two types of protein are attached to the coating comprising one or more synthetic and/or natural lipids and/or lipid membranes. In certain aspects, the Signal 1 protein and the Signal 2 protein are present on the particle in a 1:1 molar ratio.

In yet other aspects, the presently disclosed subject matter provides a method for treating a disease or condition in subject in need of treatment thereof, the method comprising administering to the subject a therapeutically effective amount of the presently disclosed biodegradable particle. In certain aspects, the disease or condition comprises type 1 diabetes.

In other aspects, the presently disclosed subject matter provides a method for modulating an immune response in a subject, the method comprising administering an effective amount of a presently disclosed biodegradable particle. In certain aspects, the subject is afflicted with an autoimmune disease.

In further aspects, the presently disclosed subject matter provides a kit comprising the presently disclosed biodegradable particle.

Certain aspects of the presently disclosed subject matter having been stated hereinabove, which are addressed in whole or in part by the presently disclosed subject matter, other aspects will become evident as the description proceeds when taken in connection with the accompanying Examples and Figures as best described herein below.

BRIEF DESCRIPTION OF THE FIGURES

The patent or application file contains at least one drawing executed in color. Copies of this patent or patent application publication with color drawings will be provided by the Office upon request and payment of the necessary fee.

Figure 1:
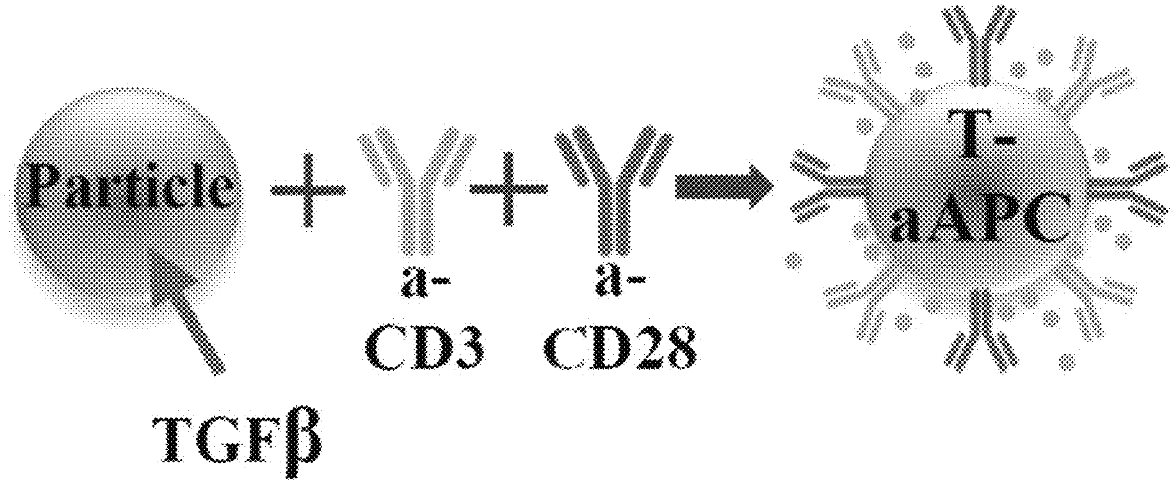
Figure 2:
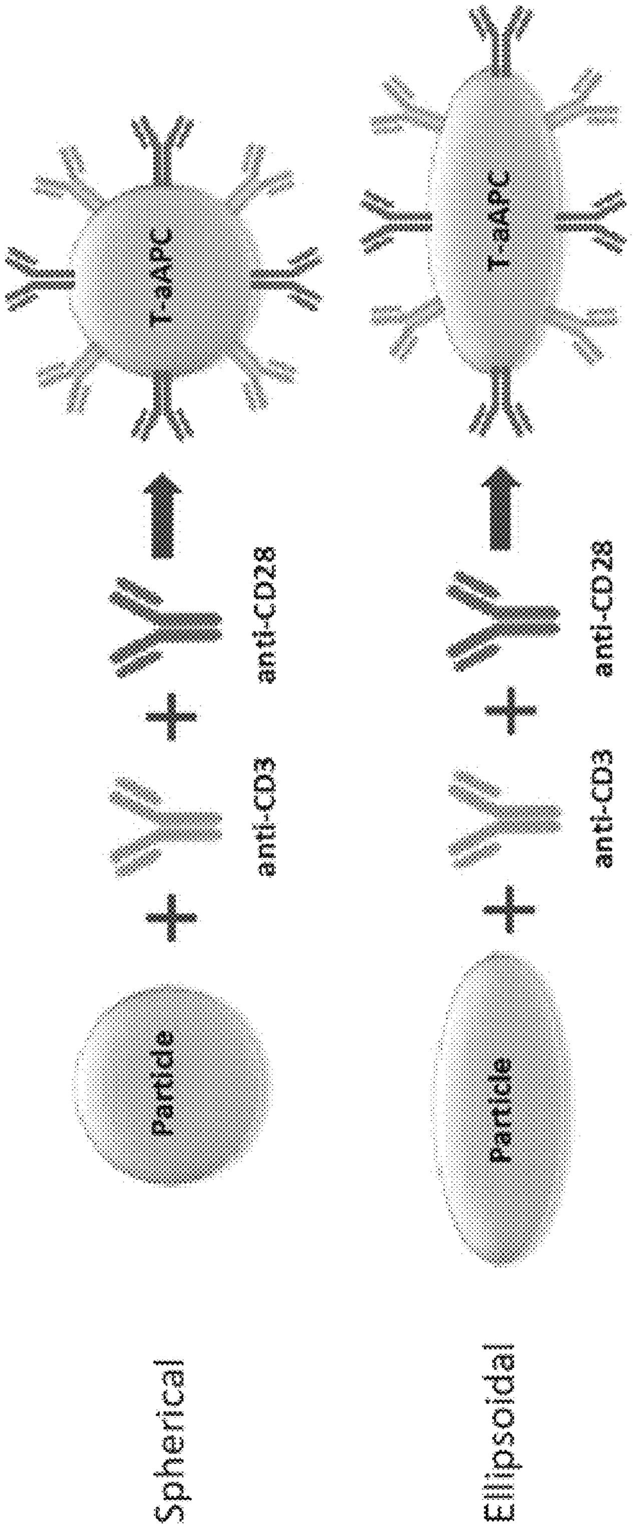
Figure 3A:
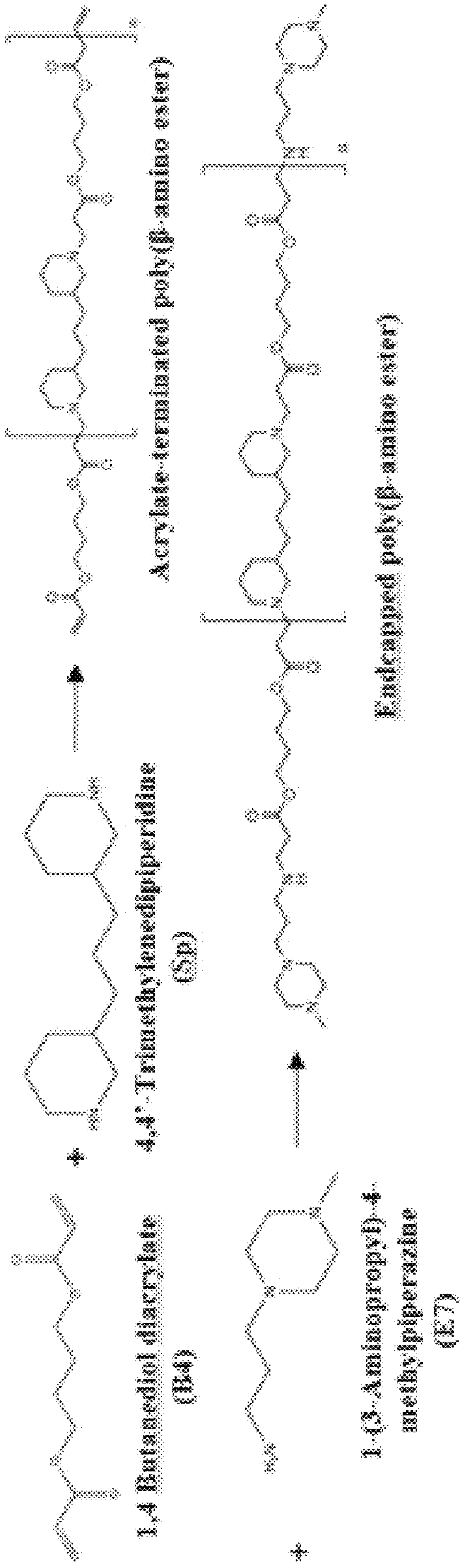
Figure 3B:
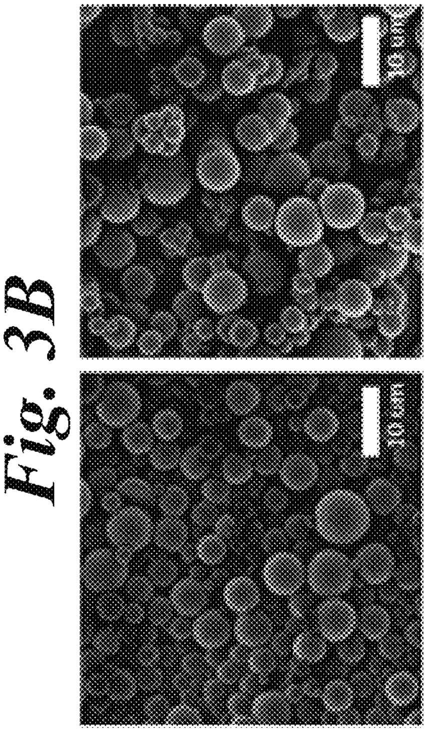
Figure 3C:
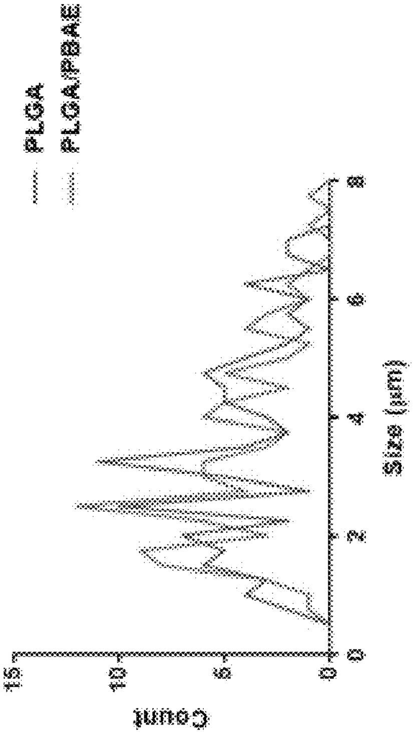
Figure 3D:
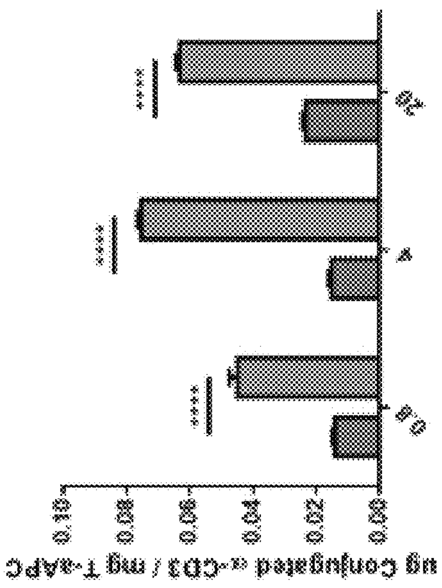
Figure 3E:
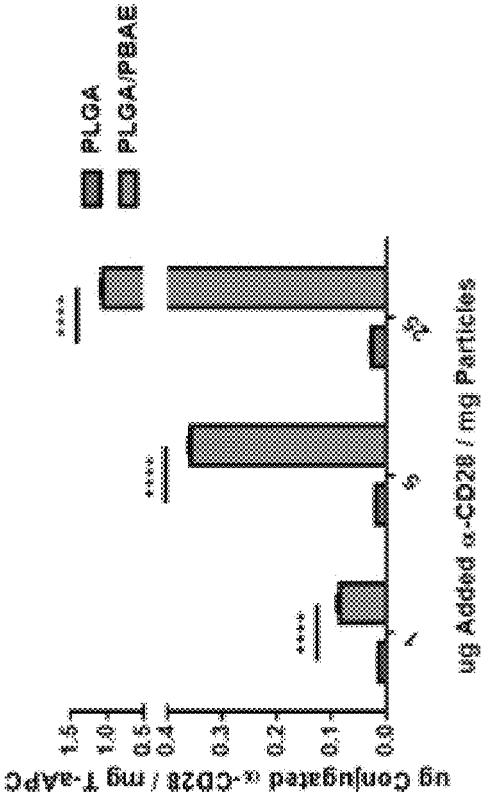
Figure 4:
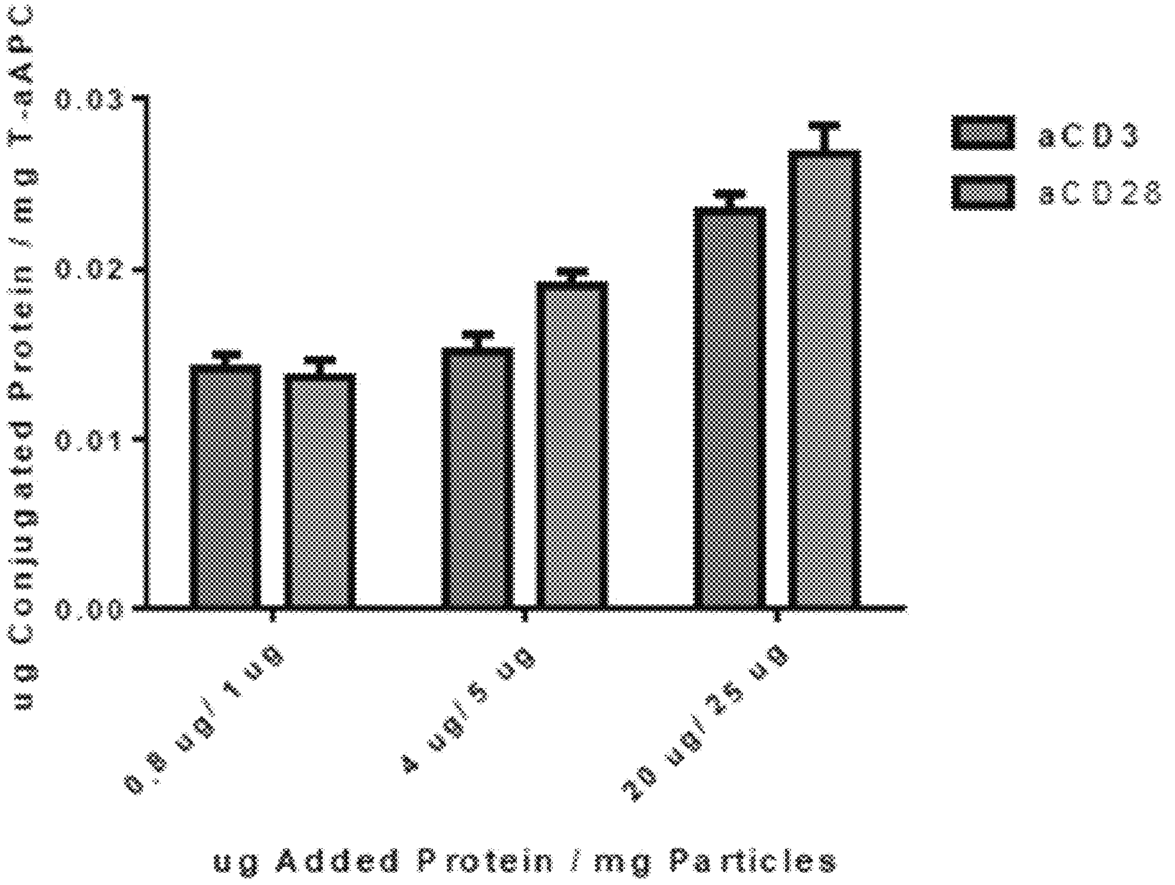
Figure 5:
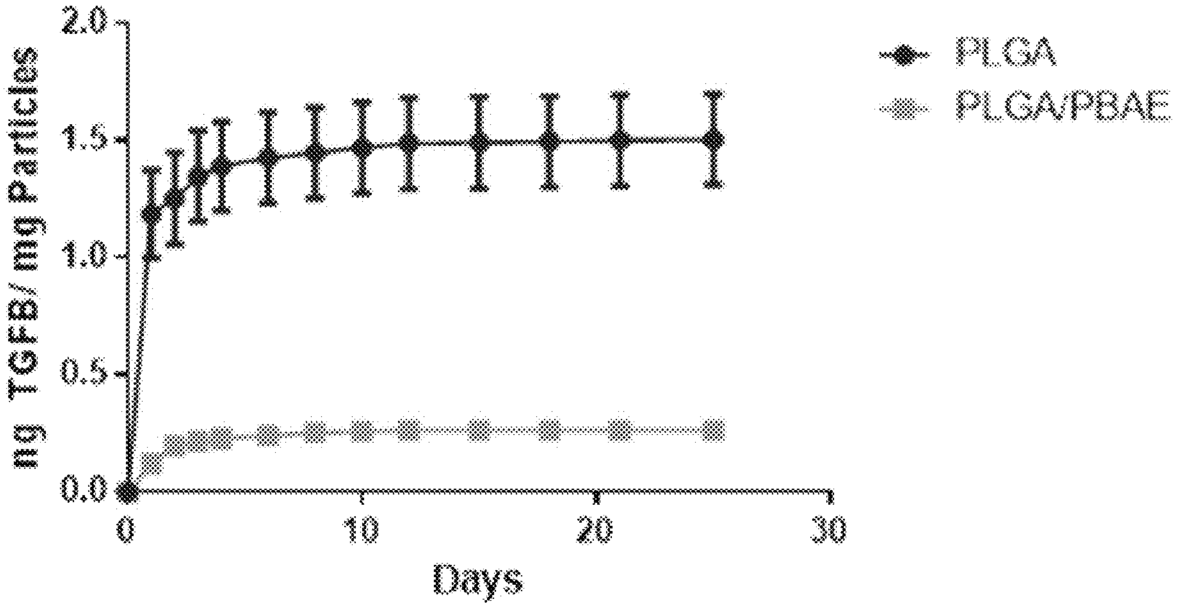
Figure 6A:
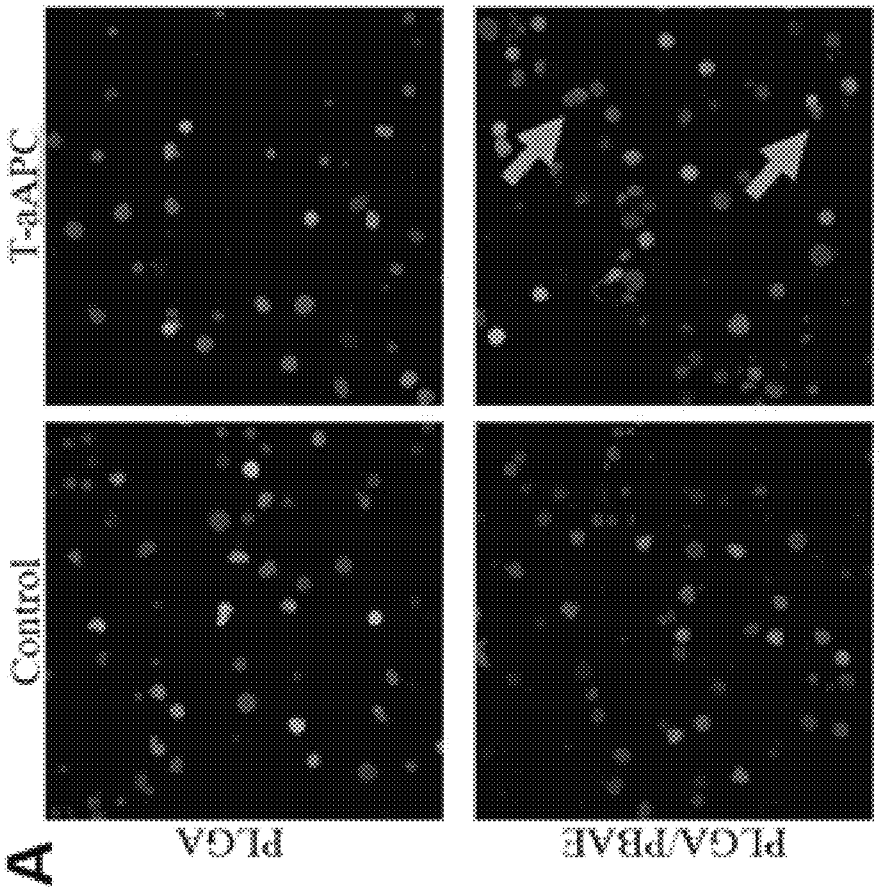
Figures 6B, 6C, 6D, 6E:
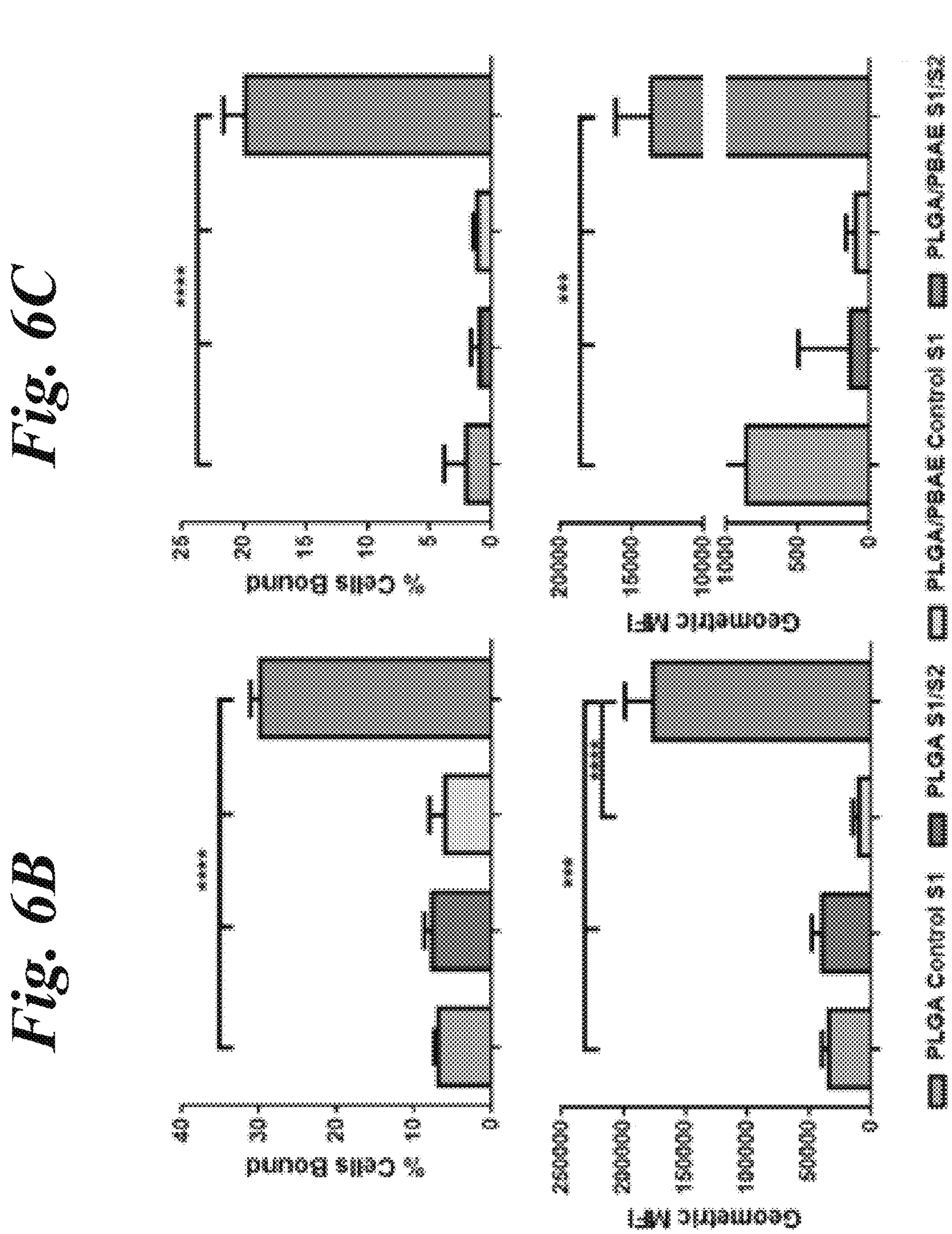
Figure 7A:
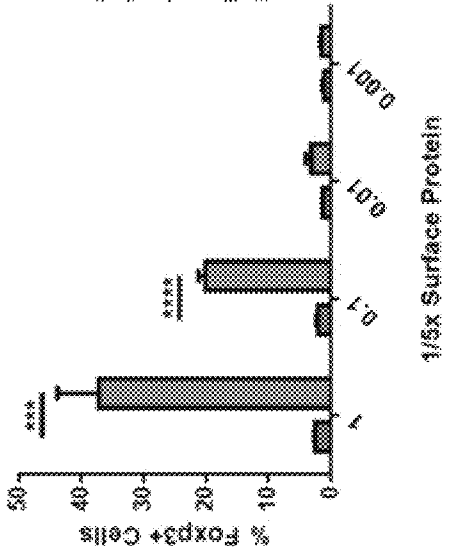
Figure 7B:
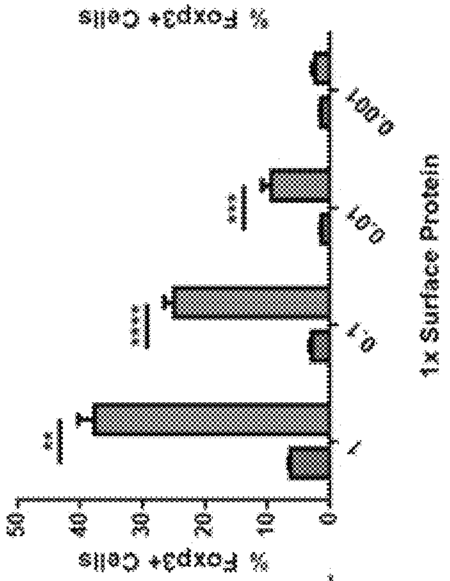
Figure 7C:
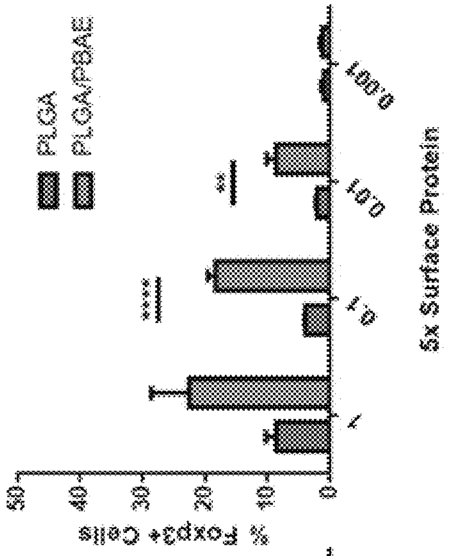

Having thus described the presently disclosed subject matter in general terms, reference will now be made to the accompanying Figures, which are not necessarily drawn to scale, and wherein:

FIG. 1 is a schematic of a biodegradable Tolerogenic artificial antigen presenting cell (abbreviated as T-aAPC or TolAPC) as disclosed herein;

FIG. 2 is a schematic for TolAPC synthesis, indicating that the particles used can have different shapes, including anisotropic shapes;

FIG. 3A, FIG. 3B, FIG. 3C, FIG. 3D, and FIG. 3E show T-aAPC synthesis and characterization;

FIG. 3A shows that PBAE was synthesized through two sequential Michael Addition reactions. First, a diacrylate-terminated base monomer was reacted in excess with a hydrophobic diamine-terminated side chain monomer to generate a diacrylate-terminated PBAE. The base PBAE polymer was then endcapped with a small amine-terminated molecule;

FIG. 3B is SEM images of PLGA (left) and PLGA/PBAE (right) microparticles reveal similar size and spherical morphology, which can be controlled to be independent of chemical composition, so that the surprising enhancement of the TolAPCs due to chemical composition (PLGA/PBAE) can be clearly observed. Scale bars indicate 10 micrometers;

FIG. 3C demonstrates that PLGA and PLGA/PBAE microparticles have similar size distributions;

FIG. 3D and FIG. 3E illustrate protein conjugation. PLGA/PBAE T-aAPCs conjugate significantly more anti-CD3 (FIG. 3D) and anti-CD28 (FIG. 3E) to their surface than PLGA T-aAPCs across a range of protein doses added during conjugation. Error bars are the SEM of five replicates. (****=$p<0.0001$);

FIG. 4 demonstrates conjugation of protein to a particle surface to construct TolAPC. Particle surfaces can be polymeric or lipid-coated. Other proteins that interact with immune cells can be similarly added chemically or physically to the particle surface;

FIG. 5 illustrates TGF-β release from PLGA and PLGA/PBAE particles. PLGA and PLGA/PBAE particles loaded with TGF-β were fabricated using a double emulsion technique and incubated at 37° C. Released TGF-β was measured using an ELISA. PLGA particles released 1.5 ng TGF-3/mg, and PLGA/PBAE particles released 0.26 ng TGF-3/mg;

FIG. 6A, FIG. 6B, FIG. 6C, FIG. 6D, and FIG. 6E show that PLGA/PBAE T-aAPCs interact more with naïve CD4+ T cells than PLGA T-aAPCs. FIG. 6A shows confocal images of fluorescent PLGA and PLGA/PBAE T-aAPC binding to fluorescently labeled naïve CD4+ T cells. Blue arrows indicate binding events; FIG. 6B and FIG. 6C show flow cytometric analysis of T-aAPC/T-cell binding. Significantly more naïve CD4+ T cells bind to PLGA/PBAE T-aAPCs than to PLGA aAPCs at 0.05 mg (FIG. 6B) and 0.01 mg doses (FIG. 6C). FIG. 6D and FIG. 6E show mean fluorescence intensity of PLGA/PBAE T-aAPC/cell complexes is significantly higher than that of PLGA T-aAPC/cell complexes, indicating that cells contain higher numbers of bound T-aAPCs at a 0.05 mg dose (FIG. 6D) and 0.01 mg dose (FIG. 6E). Error bars are the SEM of three replicates. (*=$p<0.001$, **=$p<0.0001$);

FIG. 7A, FIG. 7B, and FIG. 7C demonstrate that PLGA/PBAE T-aAPCs induce significantly more Tregs than PLGA T-aAPCs. PLGA and PLGA/PBAE T-aAPCs conjugated with FIG. 7A) ⅕x; FIG. 7B) 1x; and FIG. 7C) 5xsignal protein densities were incubated with naïve CD4+ T cells in the presence of TGF-β and IL-2 for five days, then stained for FOXP3. Enhanced induction efficacy of PLGA/PBAE T-aAPCs was seen over a range of aAPC doses. Error bars are the SEM of five replicates. (=$p<0.01$, *=$p<0.001$, ****=$p<0.0001$);

FIG. 8A, FIG. 8B, FIG. 8C, FIG. 8D, and FIG. 8E demonstrate that cell populations induced by PLGA/PBAE T-aAPCs more effectively suppress proliferation of naïve CD4+ T cells compared to those induced by PLGA T-aAPCs.

Figure 8A:
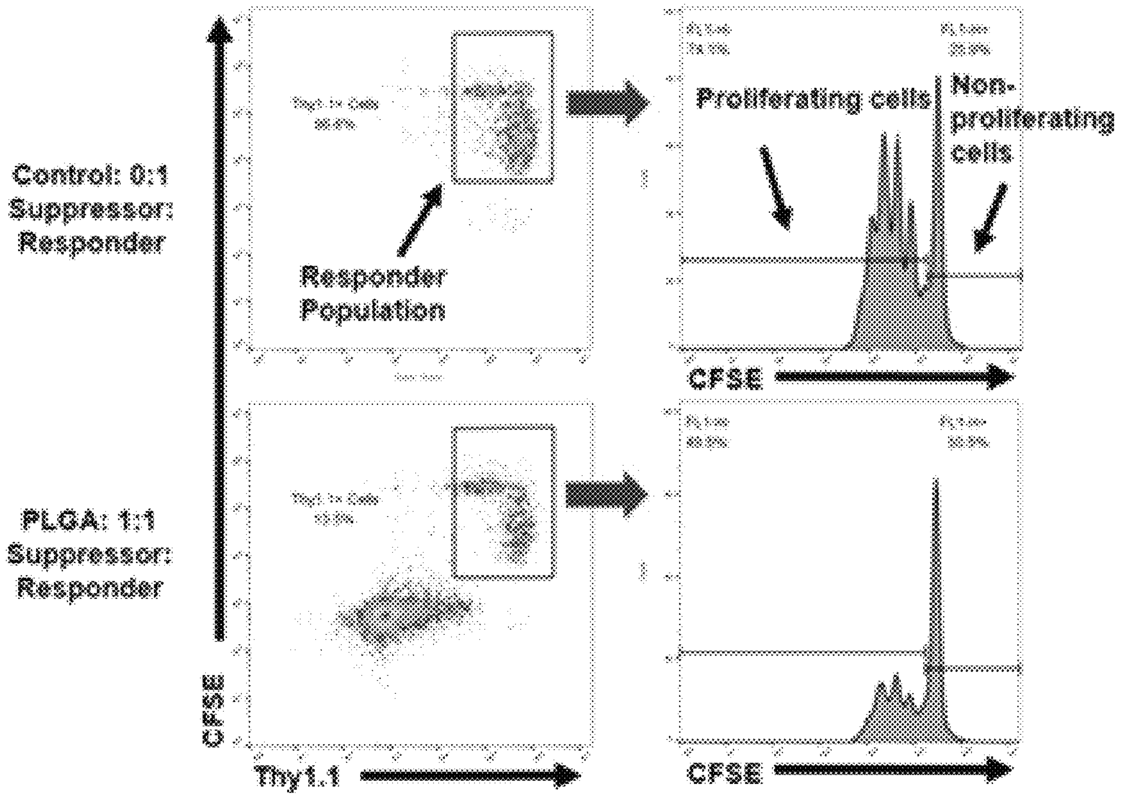
Figure 8D:
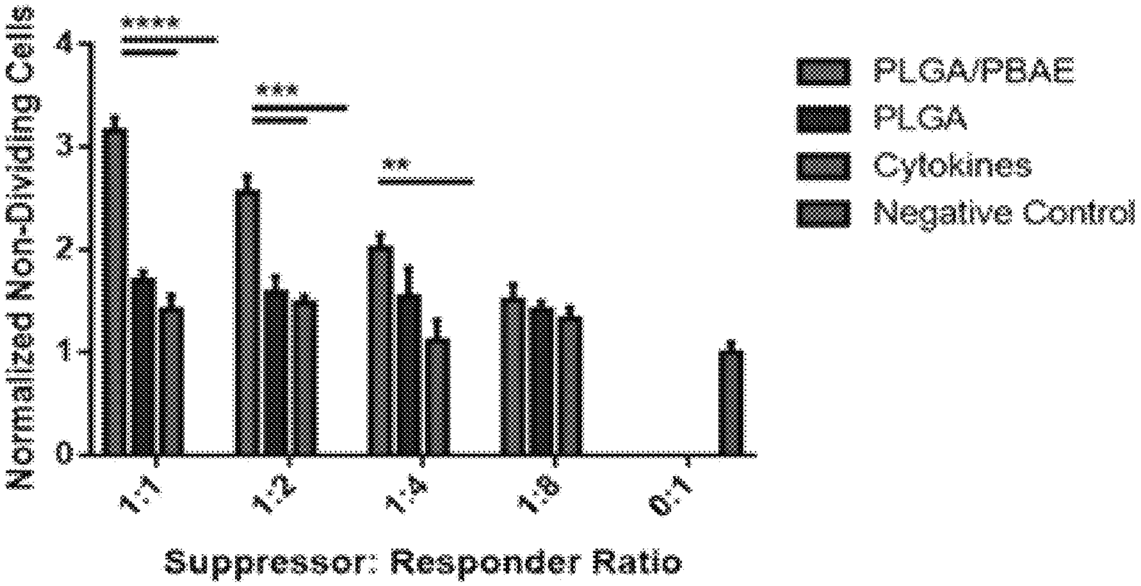
Figure 9A:
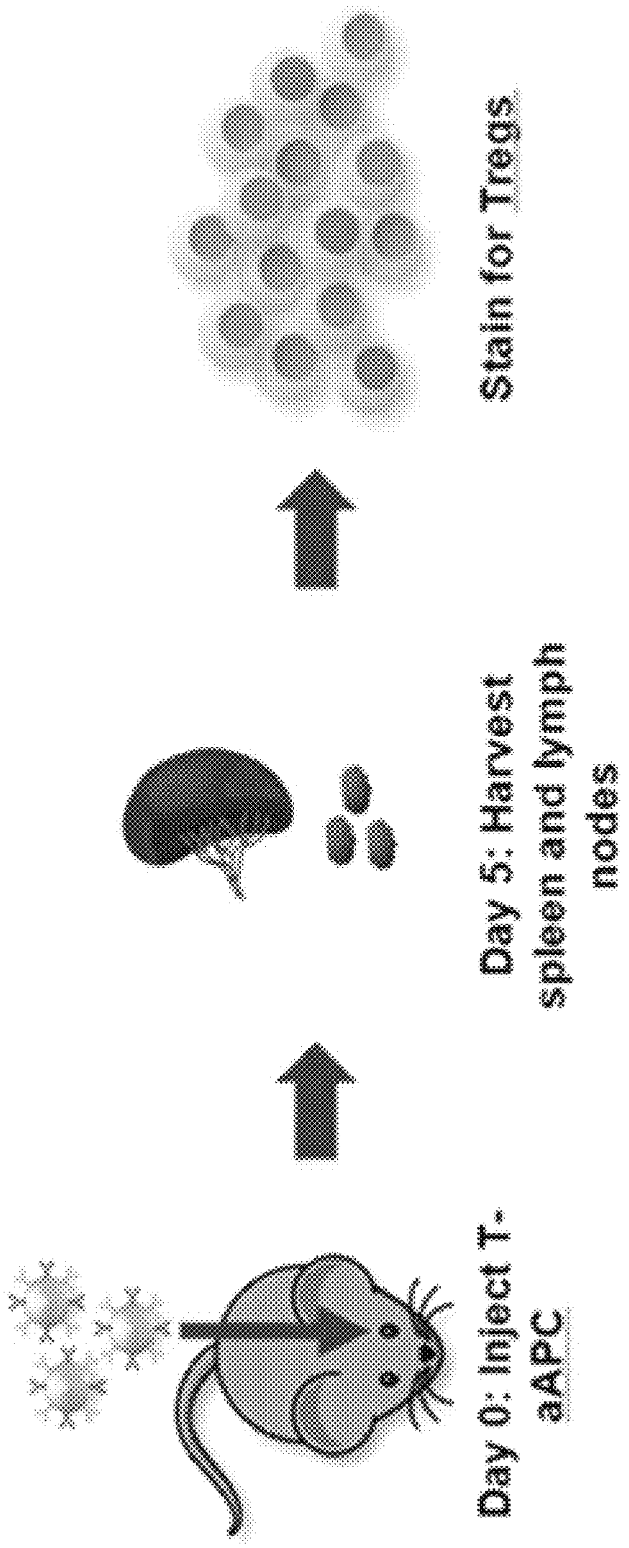
Figure 10A:
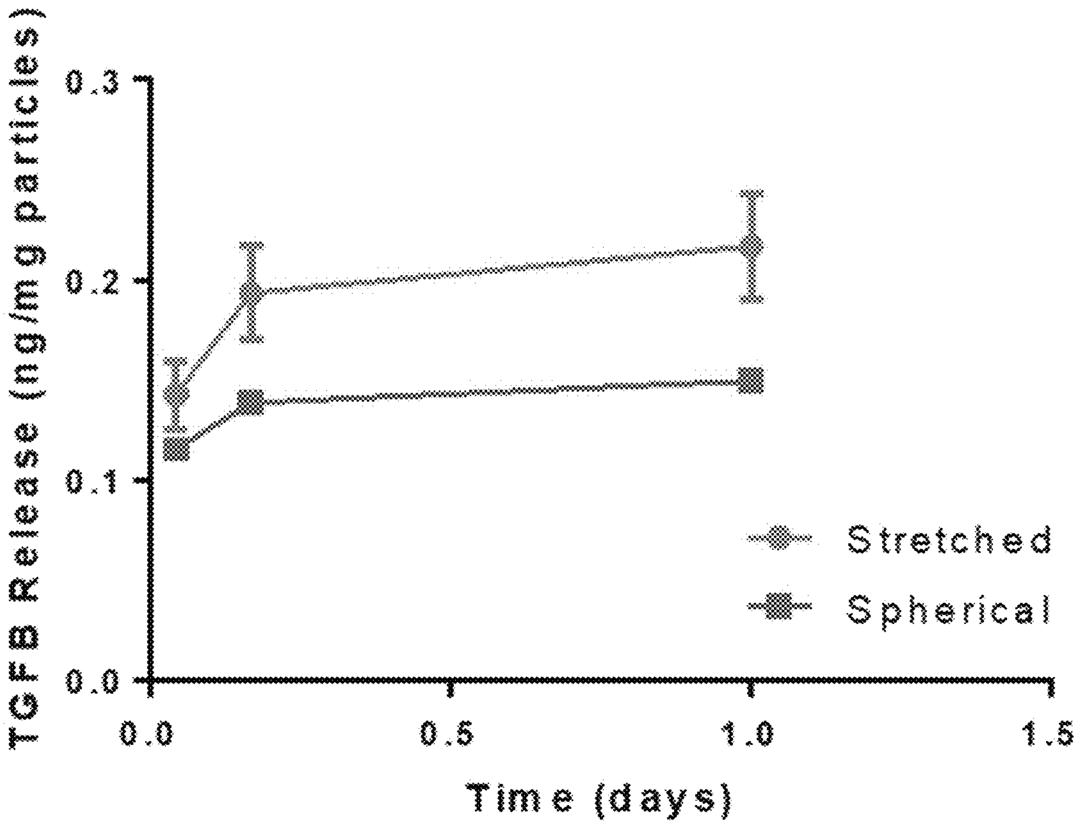
Figure 10B:
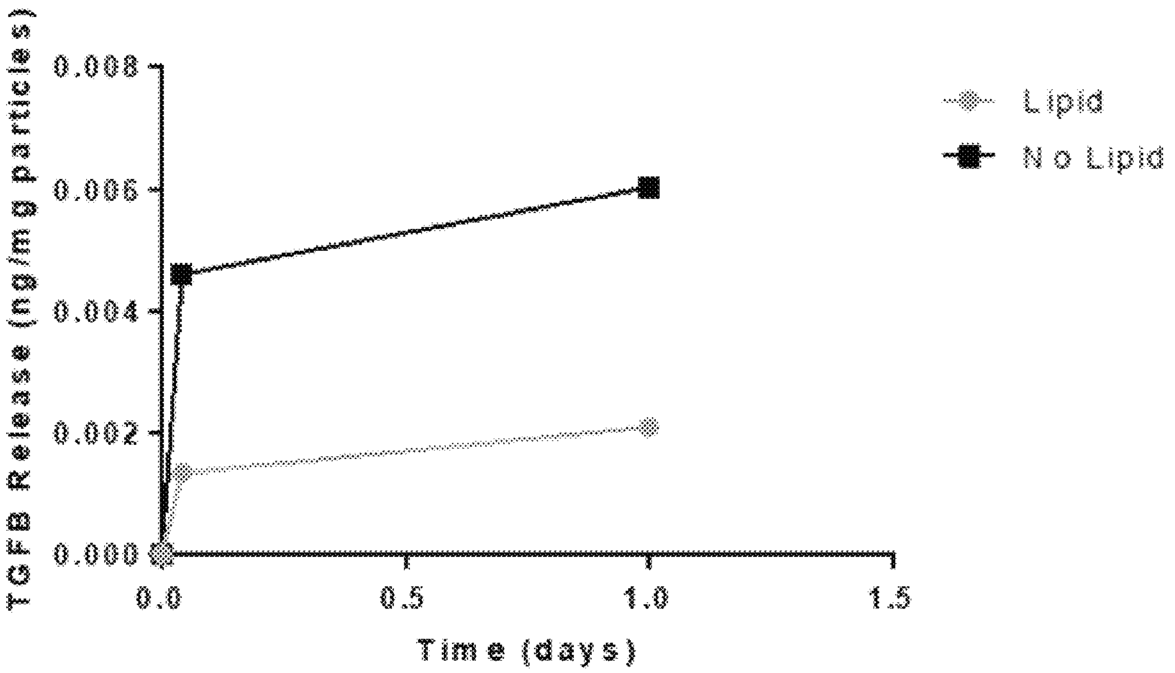
Figure 11:
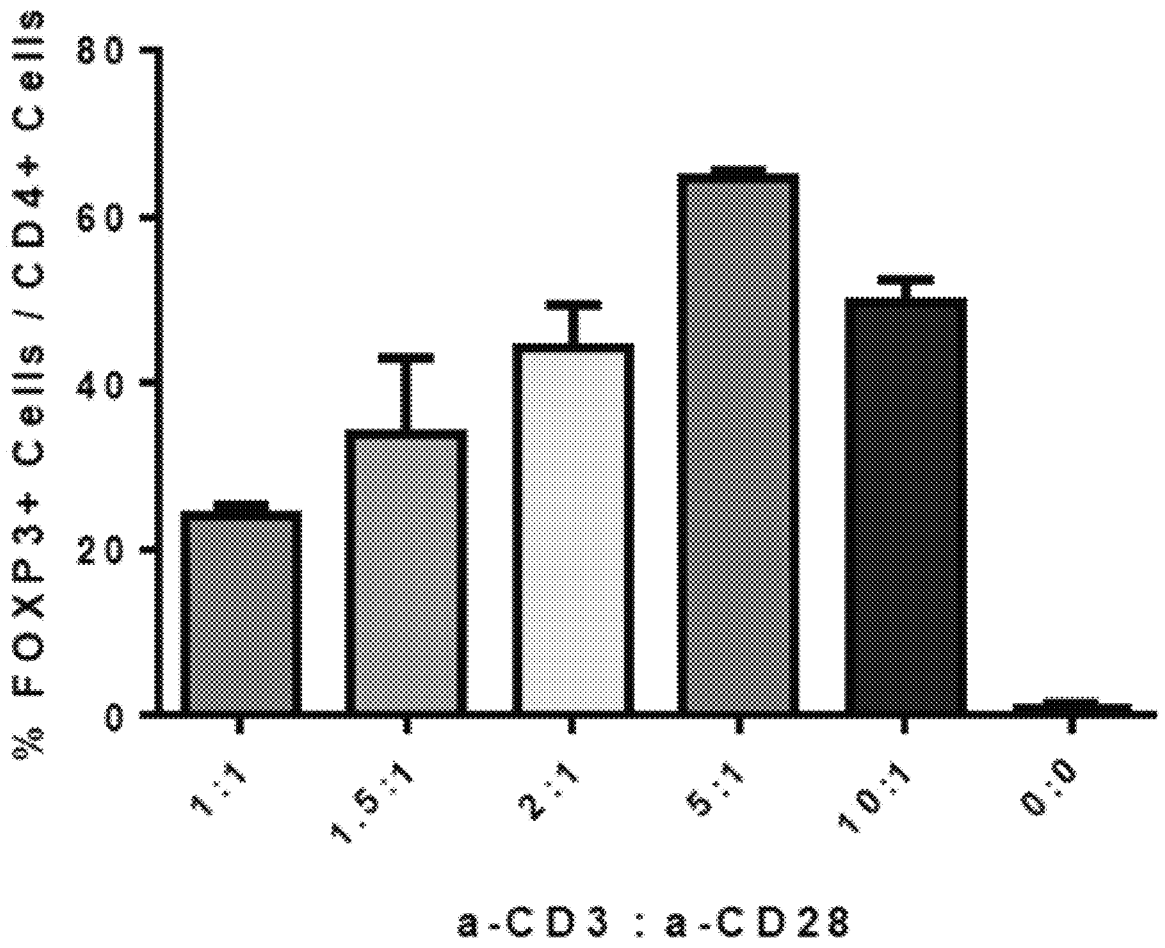
Figure 12:
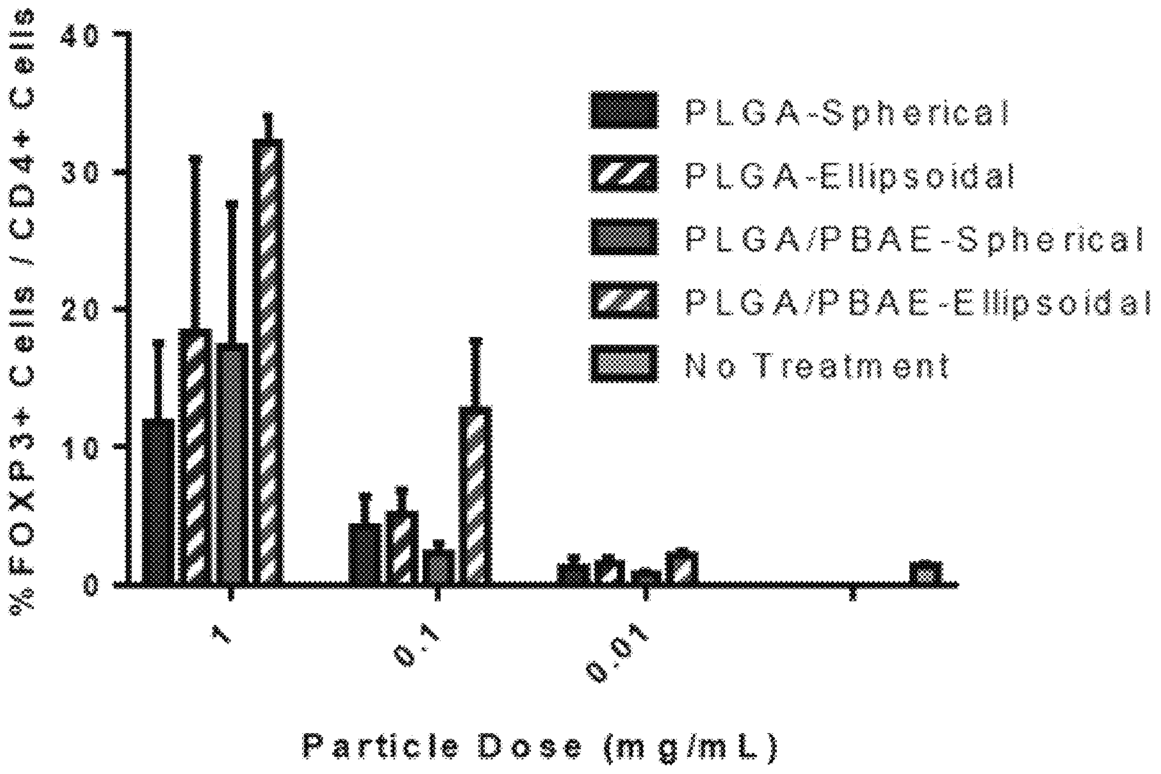
Figure 13:
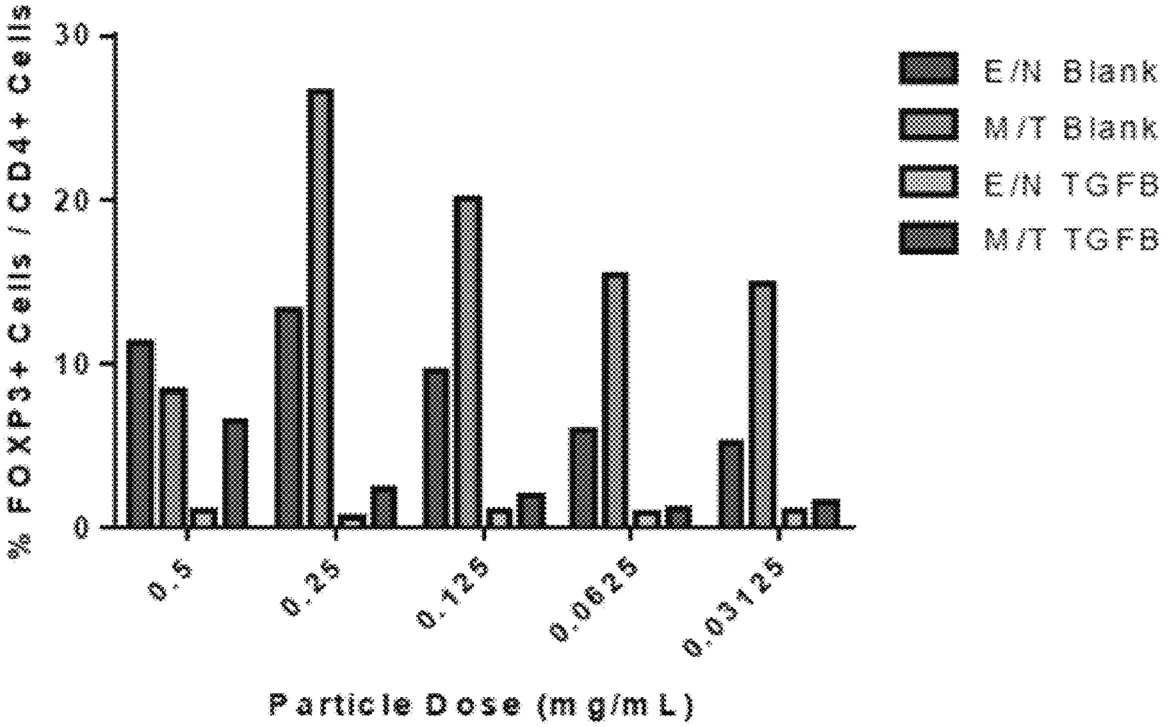
Figure 14:
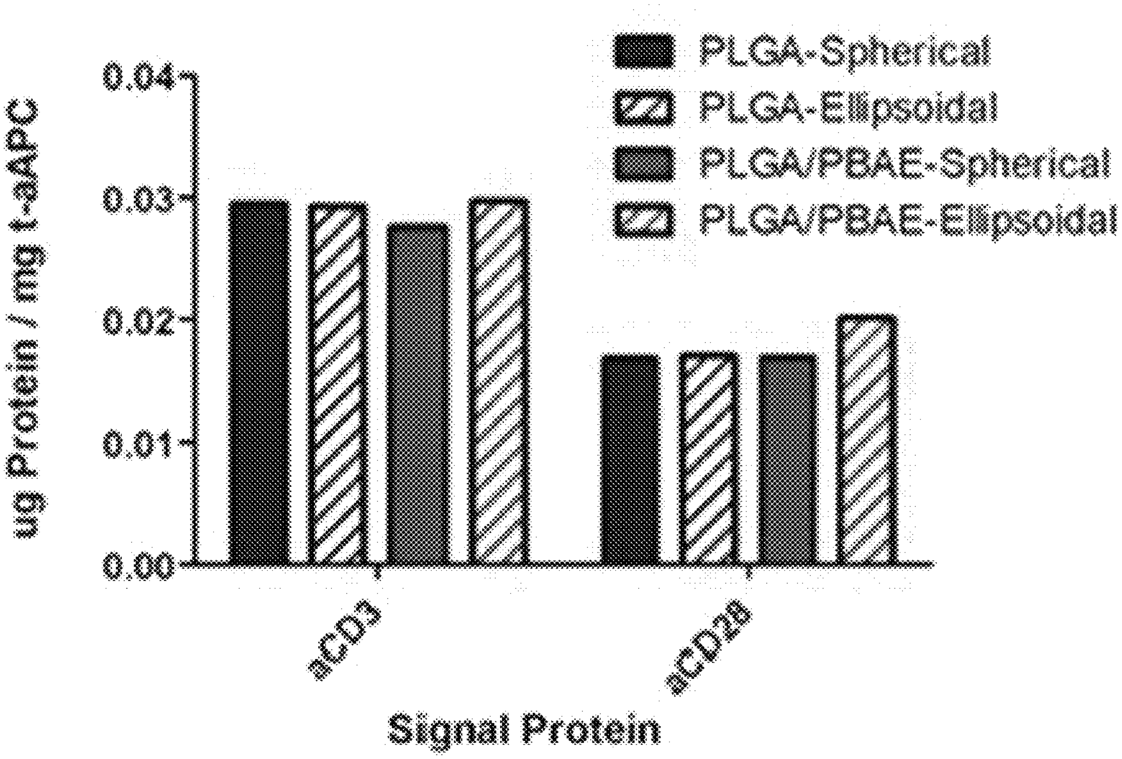
Figure 15:
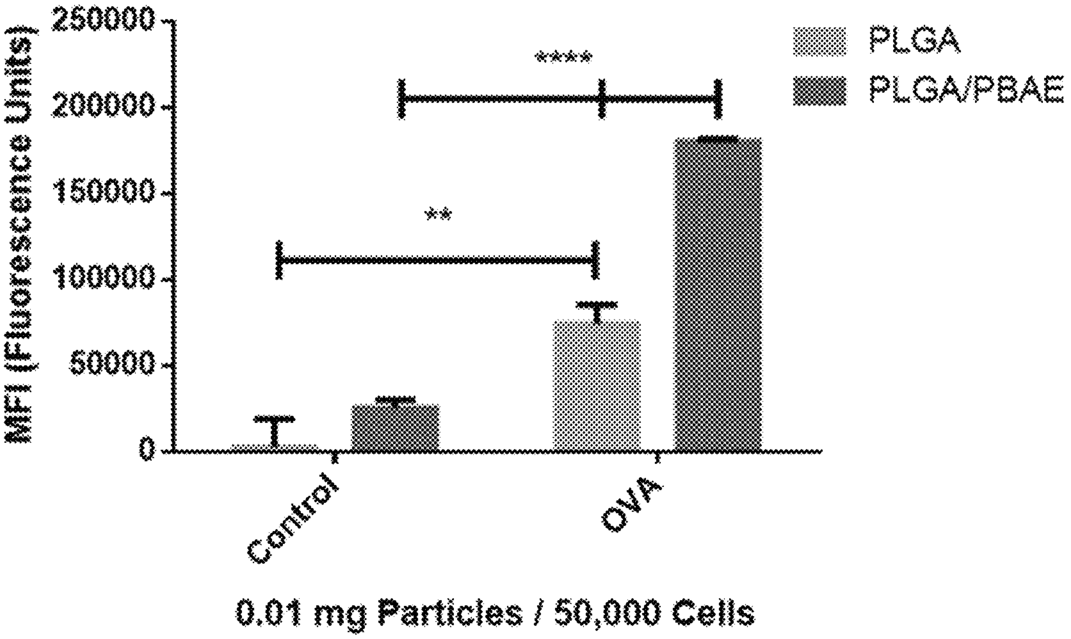
Figure 16:
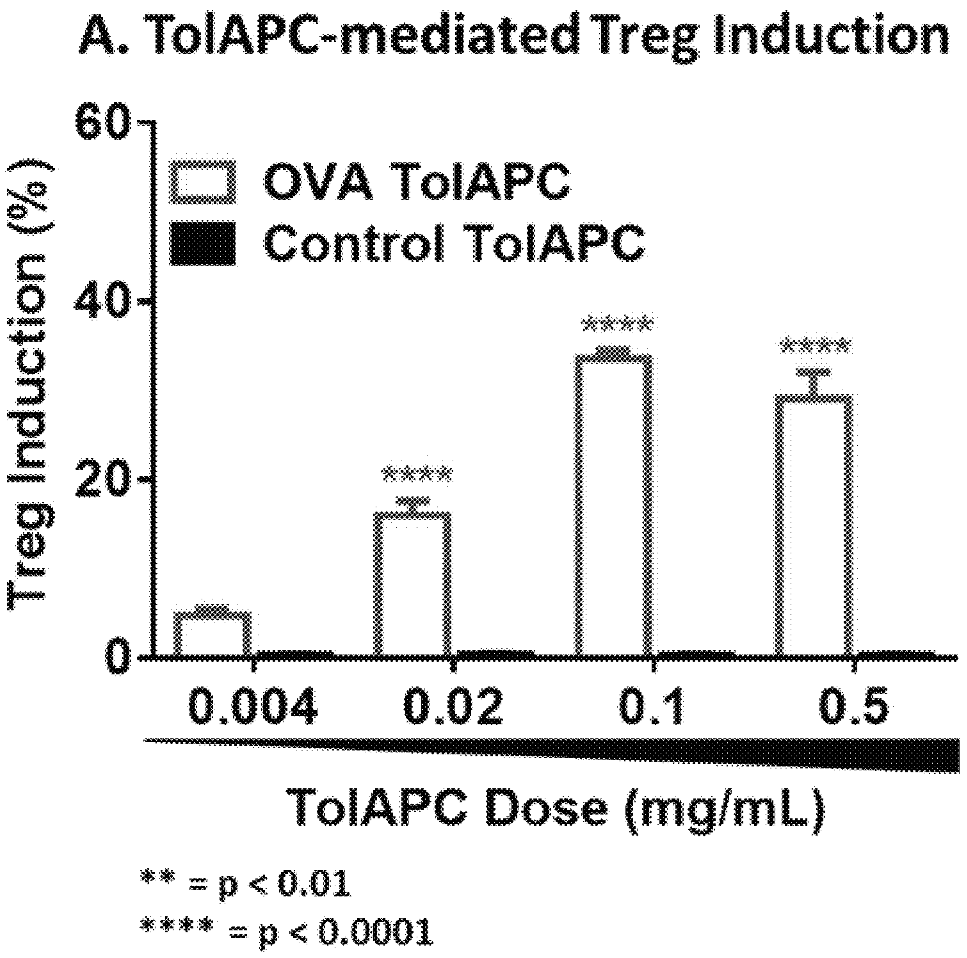
Figure 17:
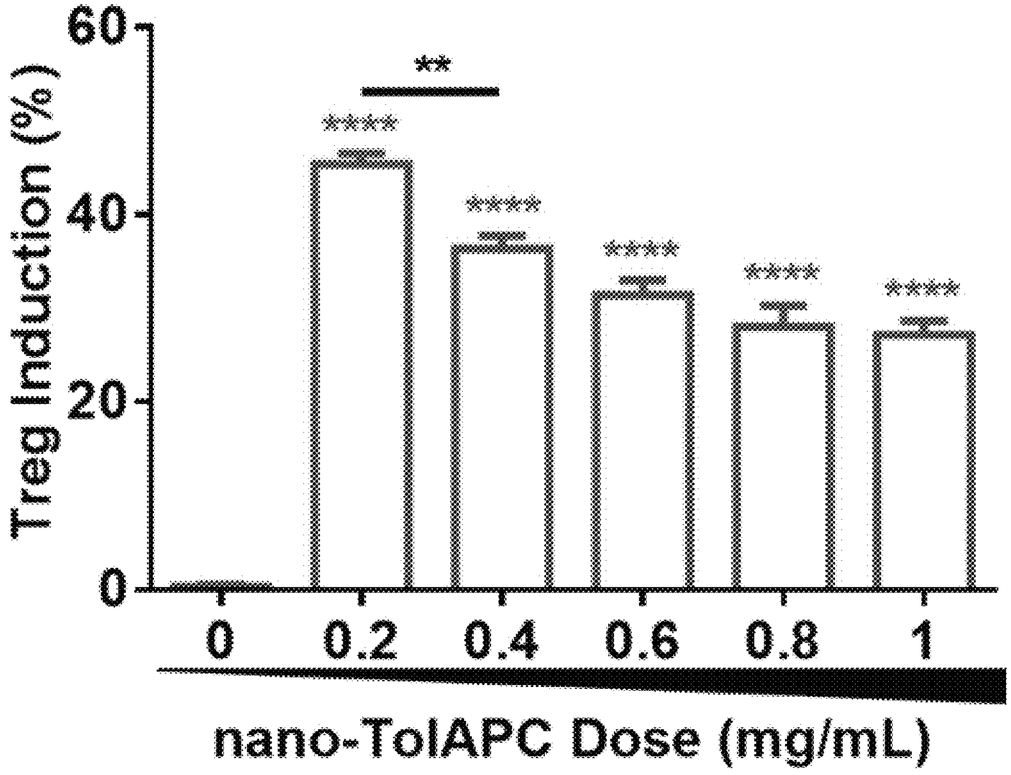
Figure 18:
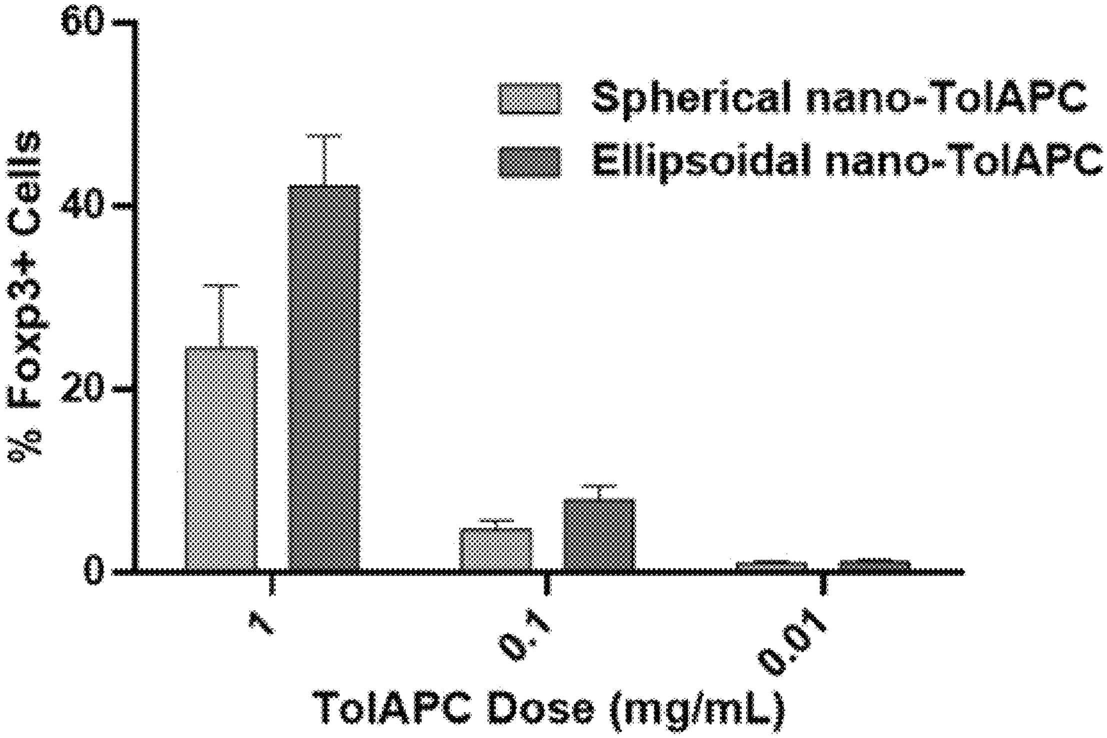
Figure 19:
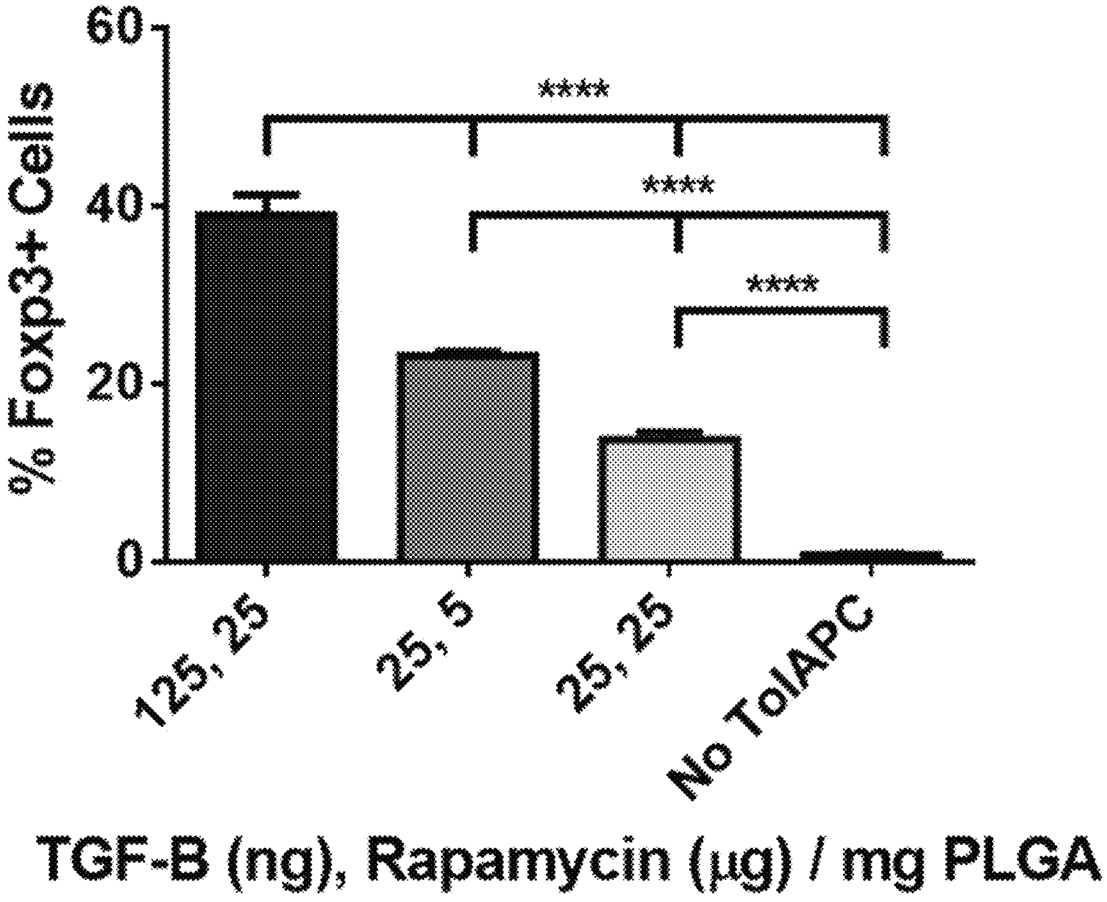

FIG. 8A illustrates a gating strategy for in vitro suppression assay. CFSE dilution peaks were used to ascertain the fractions of proliferating and nonproliferating Thy1.1+ responder cells;

FIG. 8B shows FOXP3 expression in suppressor populations after a five-day induction period with PLGA T-aAPCs, PLGA/PBAE T-aAPCs, or cytokines TGF-β and IL-2 only;

FIG. 8C shows CFSE dilution peaks of responder population at various suppressor/responder ratios. Less proliferation is seen in responder populations incubated with PLGA/PBAE T-aAPC-induced suppressor populations;

FIG. 8D demonstrates that suppressor populations induced with PLGA/PBAE T-aAPCs significantly suppress responder proliferation compared to those induced by PLGA T-aAPCs or a cytokine control at multiple suppressor-to-responder ratios. Error bars are the SEM of three replicates. ($p<0.01$, *$p<0.001$, ****$p<0.0001$);

FIG. 9A, FIG. 9B, FIG. 9C, FIG. 9D, and FIG. 9E demonstrate that PLGA/PBAE T-aAPCs more effectively induce Tregs in vivo;

FIG. 9A is an illustration depicting that T-aAPCs were injected retroorbitally into Black 6 mice. After 5 days, the spleens and lymph nodes were harvested and stained for FOXP3 expression. Fluorescence was measured using flow cytometry;

FIG. 9B and FIG. 9C show that spleens (FIG. 9B) and lymph nodes (FIG. 9C) of Black 6 mice injected with PLGA/PBAE T-aAPCs contained more Tregs than those injected with PLGA T-aAPCs. Higher levels of FOXP3 expression in FOXP3+ cells also were observed in the spleens (FIG. 9D) and lymph nodes (FIG. 9E) of mice injected with PLGA/PBAE T-aAPCs compared to those injected with PLGA T-aAPCs or control particles. Error bars represent the SEM of five replicates. (*$p<0.05$, **$p<0.01$);

FIG. 10A and FIG. 10B demonstrate release of TGF-β1 from the particles, spherical or ellipsoidal, with and without lipid coating. Other proteins or small molecules can similarly be released from the T-aAPCs;

FIG. 11 demonstrates the importance of protein ratio during conjugation of protein to particle surface, which can be polymeric or lipid before conjugation, to construct T-aAPC. (IL-2 and TGF-β1 added). Higher levels of Treg induction resulted when increased ratios of plate-bound α-CD3 to α-CD28 were presented to naïve T-cells, with the highest level of induction occurring at a 5:1 ratio;

FIG. 12 demonstrates the importance of polymer composition and shape on the activity of TolAPC (IL-2 and TGF-β1 added). TolAPC fabricated from a PLGA/PBAE blend and stretched in 1-D induced more Tregs across a range of doses than spherical and PLGA T-aPC;

FIG. 13 demonstrates the TolAPC with TGF-β1 added to media (blank) or only encapsulated within the particles (TGFB). E/N and M/T refer to different surface conjugation methods;

FIG. 14 shows α-CD3 and α-CD28 protein conjugation amount and demonstrates that protein composition can be controlled independently of chemical composition and particle shape. In this example, after adding α-CD3 and α-CD28 at a 5:1 ratio to the conjugation media, spherical and ellipsoidal PLGA and PLGA/PBAE T-aPC conjugated higher amounts of α-CD3 compared to α-CD28;

FIG. 15 is a graph showing that OVA-specific TolAPCs exhibited enhanced binding to OT-II cells. PLGA/PBAE TolAPC demonstrated significantly better binding as compared to PLGA TolAPC. Fluorescent TolAPCs were incubated with CFSE-labelled CD4+ T cells from OT-II mice for 1 hour at 37° C. and binding was assessed using flow cytometry. Statistical comparisons were performed using one-way ANOVA with Tukey's post-test using GraphPad Prism software version 6.01;

FIG. 16 is a graph showing that unloaded TolAPC surface-conjugated with OVA tetramer and anti-CD28 induced OVA-specific Tregs from naïve OT-II CD4+ T cells, while TolAPC bearing a control tetramer did not induce $T_{Reg}$ cells. Maximum $T_{Reg}$ induction was achieved at a TolAPC dose of 0.1 mg/mL. Statistical comparisons were performed using two-tailed student's t-test using GraphPad Prism software version 6.01;

FIG. 17 is a graph showing that nanoscale TolAPCs induced up to 45% ovalbumin-specific $T_{Reg}$ cells in the absence any exogenous factors. TolAPCs were incubated at varying concentrations with naïve CD4+ T cells from OT-II mice for 3 days. FOXP3 expression was analyzed by flow cytometry to assess $T_{Reg}$ cell induction. Statistical comparisons were performed using two-way ANOVA with Sidak's post-test using GraphPad Prism software version 6.01;

FIG. 18 is a graph showing that ellipsoidal nano-TolAPCs improve $T_{Reg}$ cell induction compared to spherical nano-TolAPCs at a 1 mg/mL dose. TolAPCs were incubated with naïve CD4+ T cells from OT-II mice for 3 days, and then stained for FOXP3 to assess $T_{Reg}$ cell induction; and FIG. 19 is a graph showing $T_{Reg}$ cell induction by OVA-TolAPCs loaded with different amounts of TGF-β and rapamycin. A 100 μg/mL dose of OVA-TolAPCs was used to induce $T_{Reg}$ cells from naïve OT-II $CD4^+$ T cells. A loading dose of 125 ng TGF-β and 25 μg rapamycin/mg PLGA during TolAPC synthesis was found to be most effective for $T_{Reg}$ cell induction. Statistical comparisons were performed using one-way ANOVA with Tukey's post-test using GraphPad Prism software version 6.01.

DETAILED DESCRIPTION

The presently disclosed subject matter now will be described more fully hereinafter with reference to the accompanying Figures, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the appended claims.

I. Tolerogenic Artificial Antigen-Presenting Cells

A. Biodegradable Particle-Based Tolerogenic Artificial Antigen Presenting Cells

The presently disclosed subject matter provides biodegradable particles for interacting with immune cells to generate an immunosuppressive effect. More particularly, the presently disclosed subject matter provides biodegradable particle-based tolerogenic artificial antigen presenting cells (also referred to herein as "TolAPC" or "T-aAPC," which are used interchangeably herein) which can be used to induce Tregs in vitro and in vivo for autoimmune therapy. As used herein, "Tregs" are a subpopulation of T cells that modulate the immune system, maintain tolerance to self-antigens, and prevent autoimmune disease.

The presently disclosed TolAPCs can successfully interact with only those Tregs that recognize the same self-antigens that are displayed by the particles and recognized by only disease-causing cytotoxic T cells. Although primarily used in an immunostimulatory capacity, artificial antigen presenting cells (aAPC) can recapitulate the interaction between tolerogenic antigen presenting cells and naïve CD4+ cells, thereby directing T cells toward a regulatory phenotype. As used herein, an "artificial antigen presenting cell" (aAPC) is an artificial biomimetic particle-based platform that has been made in vitro and has not been made naturally by a body. As used herein, "naïve cells" are cells that have not been activated by or exposed to the selected antigen. An "antigen" as used herein is a substance that binds specifically to its respective antibody. Each antibody binds a specific antigenic structure by means of its variable complementarity determining region (CDR) interaction.

Representative embodiments of artificial antigen presenting cells are provided in U.S. Patent Application Publication No. 20180256745 for Biomimetic Artificial Cells: Anisotropic Supported Lipid Bilayers on Biodegradable Micro and Nanoparticles for Spatially Dynamic Surface Biomolecule Presentation, to Meyer et al., published Sep. 13, 2018; and U.S. Patent Application No. 20140370099 for Artificial Antigen Presenting Cells Having a Defined and Dynamic Shape, to Green et al., published Dec. 18, 2014.

The presently disclosed particles can be fabricated from materials, for example, blends of polymeric materials, that are generally regarded as safe and that degrade in water. Further, the presently disclosed particles can be fabricated to selectively engage only cells specific for certain autoimmune antigens. The presently disclosed aAPC platform can be adapted in a modular fashion to generate antigen-specific Tregs against any antigen of choice, giving it potential as an "off-the-shelf" therapy for a variety of autoimmune diseases.

In various embodiments, the presently disclosed particles comprise a polyester or polyester blend with at least one soluble protein or small molecule encapsulated within the polymeric particle and at least two types of protein attached to the surface of the polymeric particle or to a coating on its surface. Exemplary polyesters comprise one or more of poly(lactic-co-glycolic acid) (PLGA), polycaprolactone (PCL), polyglycolide (PGA), poly(lactic acid) (PLA), a polyhydroxyalkanoate (PHA), such as poly-3-hydroxybutyrate (P3HB), poly(acrylic acid) (PAA), poly(3-hydroxybutyrate-co-3-hydroxyvalerate) (PHBV), a poly(beta-amino ester) (PBAE), or combinations thereof, or other hydrolytically biodegradable polymers. Accordingly, the presently disclosed biodegradable particles include one or more of the following polyesters:

(PLGA)

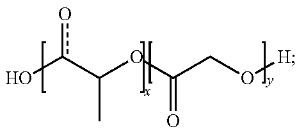

(PCL)

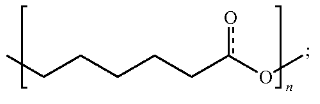

(PGA)

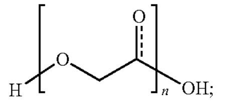

(PLA)

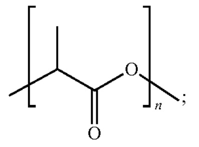

(P3HB)

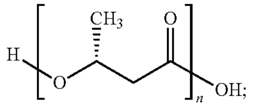

(PAA)

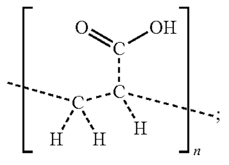

-continued (PHBV)

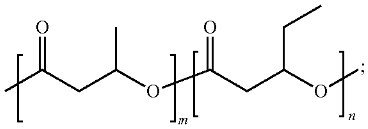

(PBAE)

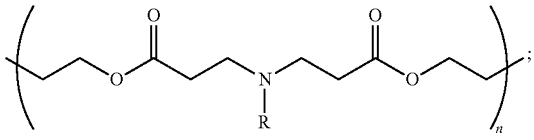

wherein each x, y, m, and n can independently be an integer from 1 to 10,000.

As used herein, "biodegradable" compounds are those that, when introduced into cells, are broken down by the cellular machinery or by hydrolysis into components that the cells can either reuse or dispose of without significant toxic effect on the cells (i.e., fewer than about 20% of the cells are killed when the components are added to cells in vitro). The components preferably do not induce inflammation or other adverse effects in vivo. In certain preferred embodiments, the chemical reactions relied upon to break down the biodegradable compounds are uncatalyzed.

In certain embodiments, the biodegradable particle comprises a material having one or more degradable linkages, such as an ester linkage, a disulfide linkage, an amide linkage, an anhydride linkage, and a linkage susceptible to enzymatic degradation. Representative degradable linkages include, but are not limited to:

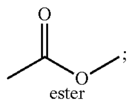

ester

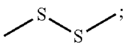

disulfide

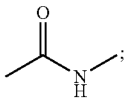

amide and

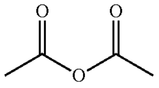

anhydride

In some embodiments, the biodegradable particle comprises a poly(lactic-co-glycolic acid) polyethylene glycol (PLGA-PEG) block copolymer. In other embodiments, the biodegradable particle comprises a poly(lactic acid)-based polymeric matrices, such as polylactic acid (PLA), poly(D,L-lactide-co-glycolide) (PLGA), and poly(D,L-lactic acid) (PDLLA). In other embodiments, the biodegradable particle comprises a copolymer of a poly(lactic acid)-based polymer and a non-poly(lactic acid)-based polymer, such as a combination of PLA and PCL. In some embodiments, blends of polyesters may be used, such as PLGA/PCL or PLGA/PBAE. In some embodiments, the PLGA content is between about 50 to about 90% with the remainder being PCL and/or PBAE. In particular embodiments, the biodegradable particle comprises a blend of PLGA and a (PBAE). In yet other embodiments, nondegradable polymers that are used in the art, such as polystyrene, are blended with a degradable polymer or polymers disclosed immediately hereinabove to create a copolymer system. Accordingly, in some embodiments, a nondegradable polymer is blended with the biodegradable polymer.

Exemplary PBAEs suitable for use with the presently disclosed subject matter include those disclosed in:

U.S. Pat. No. 9,884,118 for Multicomponent Degradable Cationic Polymers, to Green et al., issued Feb. 6, 2018;

U.S. Pat. No. 9,802,984 for Biomimetic Peptide and Biodegradable Delivery Platform for the Treatment of Angiogenesis- and Lymphangiogenesis-Dependent Diseases, to Popel et al., issued Oct. 31, 2017;

U.S. Pat. No. 9,717,694 for Peptide/Particle Delivery Systems, to Green et al., issued Aug. 1, 2017;

U.S. Pat. No. 8,992,991 for Multicomponent Degradable Cationic Polymers, to Green et al., issued Mar. 31, 2015;

U.S. Patent Application Publication No. 20180256745 for Biomimetic Artificial Cells: Anisotropic Supported Lipid Bilayers on Biodegradable Micro and Nanoparticles for Spatially Dynamic Surface Biomolecule Presentation, to Meyer et al., published Sep. 13, 2018;

U.S. Patent Application Publication No. 20180112038 for Poly(Beta-Amino Ester)-Co-Polyethylene Glycol (PEG-PBAE-PEG) Polymers for Gene and Drug Delivery, to Green et al., published Apr. 26, 2018;

U.S. Patent Application Publication No. 20170216363 for Nanoparticle Modification of Human Adipose-Derived Mesenchymal Stem Cells for Treating Brain Cancer and other Neurological Diseases, to Quinones-Hinojosa and Green, published Aug. 3, 2017;

U.S. Patent Application Publication No. 20150273071 for Bioreducible Poly (Beta-Amino Ester)s For siRNA Delivery, to Green et al., published Oct. 1, 2015;

each of which is incorporated by reference in their entirety.

In particular embodiments, the presently disclosed tolerogenic artificial antigen presenting cells (T-aAPCs) comprise a three-dimensional microparticle or nanoparticle having a non-spherical asymmetrical shape. In such embodiments, as the particle becomes flatter, the radius of curvature of the particle becomes larger. Conversely, as a surface on the particle becomes more curved, the radius of curvature becomes smaller. In particular embodiments, the asymmetrical shape of the three-dimensional microparticle or nanoparticle has at least one surface having a radius of curvature along at least one axis selected from one of the following ranges: (a) about 1 nm to about 10 nm; (b) about 11 nm to about 100 nm; (c) about 101 nm to about 400 nm; (d) about 401 nm to about 1 µm; (e) about 10 µm to about 20 µm; (0 about 20 µm to about 100 µm; and (g) about 101 pin to about 1 mm. In some embodiments, the particle has at least one surface that has a radius of curvature that does not include the range from about 1 micron to about 10 microns.

In certain embodiments, the asymmetrical shape of the three-dimensional microparticle or nanoparticle is defined by a dimension (a) along an x-axis, a dimension (b) along a y-axis, and a dimension (c) along a z-axis, wherein at least one of (a), (b), or (c) is not equal to at least one other dimension (a), (b), or (c).

In yet other embodiments, the three-dimensional microparticle or nanoparticle comprises an ellipsoid selected from the group consisting of: a prolate ellipsoid, wherein the dimension (a) along the x-axis is greater than the dimension (b) along the y-axis, and wherein the dimension (b) along the y-axis is equal to the dimension (c) along the z-axis, such that the prolate ellipsoid can be described by the equation $a>b=c$; a tri-axial ellipsoid, wherein the dimension (a) along the x-axis is greater than the dimension (b) along the y-axis, and wherein the dimension (b) along the y-axis is greater than the dimension (c) along the z-axis, such that the tri-axial ellipsoid can be described by the equation a>b>c; and an oblate ellipsoid, wherein the dimension (a) along the x-axis is equal to the dimension (b) along the y-axis, and wherein the dimension (b) along the y-axis is greater than the dimension (c) along the z-axis, such that the oblate ellipsoid can be described by the equation a=b>c.

In some embodiments, the microparticle or nanoparticle has an aspect ratio ranging from about 1.1 to about 5, including about 1.1, 1.5, 2.0, 2.5, 3.0, 3.5, 4.0, and 4.5 to about 5.

In some embodiments, the T-aAPC has a three-dimensional shape that mimics a shape of a cell or a microorganism. In particular embodiments, the cell or a microorganism is selected from the group consisting of a bacterium, an archaeon, a protozoan, a fungus, an algae, and a virus. In yet more particular embodiments, the cell or microorganism has a shape selected from the group consisting of a spiral, a cube, a rod, a comma, a star, a square, a column, a polyhedran, a helix, an icosahedran, a cylinder, a tetrahedron, and a pyramid.

In certain embodiments, as described in part hereinabove, the three-dimensional microparticle or nanoparticle comprises a material having one or more of the following characteristics: (i) one or more degradable linkages, as defined hereinabove; (ii) a stretchable modulus; and (iii) a glass transition temperature such that the material comprising the three-dimensional microparticle or nanoparticle is a solid at room temperature and/or body temperature.

As used herein, "glass transition temperature" refers to the temperature at which amorphous polymers undergo a transition from a rubbery, viscous amorphous liquid, to a brittle, glassy amorphous solid. As used herein, "Young's modulus of elasticity" quantifies the elasticity of the polymer. It is defined, for small strains, as the ratio of rate of change of stress to strain.

As used herein, the term "nanoparticle," refers to a particle having at least one dimension in the range of about 1 nm to about 1000 nm, including any integer value between 1 nm and 1000 nm (including about 1, 2, 5, 10, 20, 50, 60, 70, 80, 90, 100, 200, 500, and 1000 nm and all integers and fractional integers in between). In some embodiments, the nanoparticle has at least one dimension, e.g., a diameter, of about 100 nm. In some embodiments, the nanoparticle has a diameter of about 200 nm. In other embodiments, the nanoparticle has a diameter of about 500 nm.

In yet other embodiments, the nanoparticle has a diameter of about 1000 nm (1 μm). In such embodiments, the particle also can be referred to as a "microparticle." Thus, the term "microparticle" includes particles having at least one dimension in the range of about one micrometer (1 μm), i.e., 1×10-6 meters, to about 1000 μm. The term "particle" as used herein is meant to include nanoparticles and microparticles.

Exemplary proteins conjugated to the surface includes a "Signal 1" protein that binds to immune cells, and in particular T cells, such as anti-CD3, MHC-peptide complex, including MHC-I and MHC-II molecules, or other TCR binder, as well as a "Signal 2" protein that acts as a co-stimulatory molecule to immune cells, and in particular T cells, such as anti-CD28, 4-1BBL, CD80, CD86, and OX40L.

More particularly, "co-stimulatory molecule," as the term is used herein, includes a molecule on an antigen presenting cell (e.g., an aAPC or T-aAPC) that specifically binds a cognate co-stimulatory molecule on a T cell, thereby providing a signal which mediates a T cell response, including, but not limited to, proliferation, activation, differentiation, and the like. A co-stimulatory molecule can include, but is not limited to, anti-CD28, CD7, B7-1 (CD80), B7-2 (CD86), PD-L1, PD-L2, 4-1BBL, OX40L, inducible costimulatory ligand (ICOS-L), intercellular adhesion molecule (ICAM), CD30L, CD40, CD70, CD83, HLA-G, MICA, MICB, HVEM, lymphotoxin beta receptor, 3/TR6, ILT3, ILT4, HVEM, an agonist or antibody that binds Toll ligand receptor and a ligand that specifically binds with B7-H3. A co-stimulatory molecule also encompasses, inter alia, an antibody that specifically binds with a co-stimulatory molecule present on a T cell, such as, but not limited to, CD27, CD28, 4-1BB, OX40, CD30, CD40, PD-1, ICOS, lymphocyte function-associated antigen-1 (LFA-1), CD2, CD7, LIGHT, NKG2C, B7-H3, and a ligand that specifically binds with CD83.

A "co-stimulatory signal", as used herein, refers to a signal that leads to T cell proliferation and/or upregulation or downregulation of key molecules.

Exemplary proteins encapsulated within the polymer includes interleukins and cytokines, such as the transforming growth factor (TGF) beta family of cytokines, including TGF-β1, TGF-β2, TGF-β3, and TGF-β4. Representative interleukins include, but are not limited to, IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IL-34, IL-35, and IL-36.

In some embodiment, the small molecule encapsulated within the particle comprises rapamycin, or an analog thereof, e.g., a rapalog, which inhibits activation of T cells and B cells by reducing their sensitivity to IL-2 through mammalian target of rapamycin (mTOR) inhibition. Representative analogs of rapamycin include, but are not limited to temsirolimus (a prodrug of rapamycin), everolimus, and ridaforolimus.

In some embodiments, the particle has a coating comprising one or more synthetic and/or natural lipids and/or lipid membranes. In particular embodiments, the at least two types of protein are attached to the coating comprising one or more synthetic and/or natural lipids and/or lipid membranes. Representative lipids suitable for use in coating the presently disclose particles include, but are not limited to, fatty acids, glycerolipids, glycerophospholipids, sphingolipids, sterol lipids, prenol lipids, saccharolipids, and polyketides.

In other embodiments, the presently disclosed subject matter provides a kit comprising a presently disclosed T-aAPC. In general, a presently disclosed kit contains some or all of the components, reagents, supplies, and the like to practice a method according to the presently disclosed subject matter. In some embodiments, the term "kit" refers to any intended article of manufacture (e.g., a package or a container) comprising a presently disclosed biodegradable particle formulation. In some embodiments, the kit can be packaged in a divided or undivided container, such as a carton, bottle, ampule, tube, etc. The presently disclosed compositions can be packaged in dried, lyophilized, or liquid form. Additional components provided can include vehicles for reconstitution of dried components. Preferably all such vehicles are sterile and apyrogenic so that they are suitable for injection into a patient without causing adverse reactions. The kit can further include instructions for use.

B. Methods of Treating an Autoimmune Disease

The presently disclosed TolAPCs can be useful for treating multiple autoimmune diseases in a modular, flexible way. For example, in type 1 diabetes (T1D), incorrect information is sent to target immune cells, generating an autoimmune response that destroys pancreatic islet β cells. To alleviate this disease, the presently disclosed biodegradable particles can be designed as artificial, synthetic cells to reprogram the immune response to not attack and actively defend the pancreatic islet β cells. Selective induction and expansion of these diabeto-protective Tregs will allow them to act as an army of protectors to effectively shield the pancreatic islet β cells from harm to allow for normal and healthy insulin production.

More generally, as used herein the disease or condition to be treated can be immune disorder. As used herein, the term "immune disorders" includes diseases involving the immune system that can include but not be limited to allergies, autoimmune diseases, immune complex diseases, immunodeficiency diseases and cancers of the immune system. Autoimmunity is the failure of an organism to recognize its own constituent parts (down to the sub-molecular levels) as "self," which results in an immune response against its own cells and tissues. Any disease that results from such an aberrant immune response is termed an autoimmune disease. An unwanted immune response may be, for example, immune responses associated with an autoimmune disorder, transplants, allergies, or inflammatory disorders.

Exemplary autoimmune diseases and disorders that may be treated with the presently disclosed methods include, for example, inflammatory responses, such as inflammatory skin diseases, including psoriasis and dermatitis (e.g., atopic dermatitis); dermatomyositis; systemic scleroderma and sclerosis; responses associated with inflammatory bowel disease (such as Crohn's disease and ulcerative colitis); respiratory distress syndrome (including adult respiratory distress syndrome; ARDS); dermatitis; meningitis; encephalitis; uveitis; colitis; glomerulonephritis; allergic conditions, such as eczema and asthma, and other conditions involving infiltration of T cells and chronic inflammatory responses; atherosclerosis; leukocyte adhesion deficiency; rheumatoid arthritis; systemic lupus erythematosus (SLE); diabetes mellitus (e.g. Type I diabetes mellitus or insulin dependent diabetes mellitus); multiple sclerosis; Reynaud's syndrome; autoimmune thyroiditis; allergic encephalomyelitis; Sjogren's syndrome; juvenile onset diabetes; and immune responses associated with acute and delayed hypersensitivity mediated by cytokines and T-lymphocytes typically found in tuberculosis, sarcoidosis, polymyositis, granulomatosis and vasculitis; pernicious anemia (Addison's disease); diseases involving leukocyte diapedesis; central nervous system (CNS) inflammatory disorder; multiple organ injury syndrome; hemolytic anemia (including, but not limited to cryoglobinemia or Coombs positive anemia); myasthenia gravis; antigen-antibody complex mediated diseases; anti-glomerular basement membrane disease; antiphospholipid syndrome; allergic neuritis; Graves' disease; Lambert-Eaton myasthenic syndrome; pemphigoid bullous; pemphigus; autoimmune polyendocrinopathies; Reiter's disease; stiff-man syndrome; Bechet disease; giant cell arteritis; immune complex nephritis; IgA nephropathy; IgM polyneuropathies; immune thrombocytopenic purpura (ITP) or autoimmune thrombocytopenia and autoimmune hemolytic diseases, Hashimoto's thyroiditis, Wegener's granulomatosis, cold agglutinin disease associated with indolent lymphoma, acquired factor VIII inhibitors disease, and the like.

The term "immune disorders" are diseases involving the immune system that can include but not be limited to allergies, autoimmune diseases, immune complex diseases, immunodeficiency diseases and cancers of the immune system. The term "autoimmune diseases" may include but not be limited to Acute disseminated encephalomyelitis, Addison's disease, Ankylosing spondylitisis, Antiphospholipid antibody syndrome, Aplastic anemia, Autoimmune hepatitis, Autoimmune Oophoritis, Coeliac disease, Crohn's disease, Diabetes mellitus, Gestational pemphigoid, Goodpasture's syndrome, Grave's disease, Guillan-Barre syndrome, Hashimoto's disease, Idiopathic thrombocytopenic purpura, Lupus erythematosus, Multiple sclerosis, Myasthenia gravis, Opsoclonus myoclonus syndrome, Optic neuritis, Ord's thyroiditis, Pemphigus, Pernicious anemia, Polyarthritis, Primary biliary cirrhosis, Rheumatoid arthritis, Reiter's syndrome, Sjogren's syndrome, Takayasu's arteritis, Warm autoimmune hemolytic anemia, and Wegener's granulomatosis. The term "chronic inflammatory diseases" may include but not be limited to Tuberculosis, Chronic cholecystitis, Bronchiectasis, ulcerative colitis, silicosis and other pneumoconiosis, as well as the above listed autoimmune diseases.

In particular embodiments, the disease or condition is diabetes. In yet more particular embodiments, the disease or condition is type 1 diabetes. In other embodiments, the presently disclosed TolAPCs can be useful for preventing rejection in transplantation. Thus, in such embodiments, the subject to be treated is an organ transplant recipient or a subject who is treated in advance of becoming an organ transplant recipient.

In yet more particular embodiments, the presently disclosed subject matter provides a method for modulating an immune response in a subject, the method comprising administering an effective amount of a presently disclosed biodegradable particle. In certain embodiments, the subject is afflicted with an autoimmune disease.

As used herein, the term "treating" can include reversing, alleviating, inhibiting the progression of, preventing or reducing the likelihood of the disease, disorder, or condition to which such term applies, or one or more symptoms or manifestations of such disease, disorder or condition. Preventing refers to causing a disease, disorder, condition, or symptom or manifestation of such, or worsening of the severity of such, not to occur. Accordingly, the presently disclosed compounds can be administered prophylactically to prevent or reduce the incidence or recurrence of the disease, disorder, or condition.

In general, the "effective amount" of an active agent refers to the amount necessary to elicit the desired biological response. As will be appreciated by those of ordinary skill in this art, the effective amount of an agent may vary depending on such factors as the desired biological endpoint, the agent to be delivered, the composition of the encapsulating matrix, the target tissue, and the like. As used herein, a "dose" refers to the amount of TolAPC administered to a subject that is sufficient to treat the subject for a disease, disorder, or dysfunction.

In the various embodiments described above, the TolAPC can be administered in a variety of forms depending on the desired route and/or dose. The TolAPC can be administered in a pharmaceutically acceptable carrier. As used herein, "pharmaceutically acceptable carrier" is intended to include, but is not limited to, water, saline, dextrose solutions, human serum albumin, liposomes, hydrogels, microparticles and nanoparticles.

Depending on the specific conditions being treated, the TolAPCs may be formulated into liquid or solid dosage forms and administered systemically or locally. The agents may be delivered, for example, in a timed- or sustained-low release form as is known to those skilled in the art. Techniques for formulation and administration may be found in Remington: The Science and Practice of Pharmacy (20th ed.) Lippincott, Williams & Wilkins (2000). Suitable routes may include oral, buccal, by inhalation spray, sublingual, rectal, transdermal, vaginal, transmucosal, nasal or intestinal administration; parenteral delivery, including intramuscular, subcutaneous, intramedullary injections, as well as intrathecal, direct intraventricular, intravenous, intra-articular, intra-sternal, intra-synovial, intra-hepatic, intralesional, intracranial, intraperitoneal, intranasal, or intraocular injections or other modes of delivery.

While the form and/or route of administration can vary, in some embodiments the TolAPC or pharmaceutical composition is administered parenterally (e.g., by subcutaneous, intravenous, or intramuscular administration), or in some embodiments is administered directly to the lungs. Local administration to the lungs can be achieved using a variety of formulation strategies including pharmaceutical aerosols, which may be solution aerosols or powder aerosols. Powder formulations typically comprise small particles. Suitable particles can be prepared using any means known in the art, for example, by grinding in an airjet mill, ball mill or vibrator mill, sieving, microprecipitation, spray-drying, lyophilization or controlled crystallization. Typically, particles will be about 10 microns or less in diameter. Powder formulations may optionally contain at least one particulate pharmaceutically acceptable carrier known to those of skill in the art. Examples of suitable pharmaceutical carriers include, but are not limited to, saccharides, including monosaccharides, disaccharides, polysaccharides and sugar alcohols such as arabinose, glucose, fructose, ribose, mannose, sucrose, trehalose, lactose, maltose, starches, dextran, mannitol or sorbitol. Alternatively, solution aerosols may be prepared using any means known to those of skill in the art, for example, an aerosol vial provided with a valve adapted to deliver a metered dose of the composition. Where the inhalable form of the active ingredient is a nebulizable aqueous, organic or aqueous/organic dispersion, the inhalation device may be a nebulizer, for example a conventional pneumatic nebulizer such as an airjet nebulizer, or an ultrasonic nebulizer, which may contain, for example, from 1 mL to 50 mL, commonly 1 mL to 10 ml, of the dispersion; or a hand-held nebulizer which allows smaller nebulized volumes, e.g. 10 μL to 100 μL.

For injection, the agents of the disclosure may be formulated and diluted in aqueous solutions, such as in physiologically compatible buffers such as Hank's solution, Ringer's solution, or physiological saline buffer.

Use of pharmaceutically acceptable inert carriers to formulate the compounds herein disclosed for the practice of the disclosure into dosages suitable for systemic administration is within the scope of the disclosure. With proper choice of carrier and suitable manufacturing practice, the compositions of the present disclosure, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the disclosure to be formulated as tablets, pills, capsules, liquids, gels, syrups, slurries, suspensions and the like, for oral ingestion by a subject (e.g., patient) to be treated.

For nasal or inhalation delivery, the agents of the disclosure also may be formulated by methods known to those of skill in the art, and may include, for example, but not limited to, examples of solubilizing, diluting, or dispersing substances such as, saline, preservatives, such as benzyl alcohol, absorption promoters, and fluorocarbons.

The "subject" treated by the presently disclosed methods in their many embodiments is desirably a human subject, although it is to be understood that the methods described herein are effective with respect to all vertebrate species, which are intended to be included in the term "subject." Accordingly, a "subject" can include a human subject for medical purposes, such as for the treatment of an existing condition or disease or the prophylactic treatment for preventing the onset of a condition or disease, or an animal subject for medical, veterinary purposes, or developmental purposes. Suitable animal subjects include mammals including, but not limited to, primates, e.g., humans, monkeys, apes, and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, and the like. An animal may be a transgenic animal. In some embodiments, the subject is a human including, but not limited to, fetal, neonatal, infant, juvenile, and adult subjects. Further, a "subject" can include a patient afflicted with or suspected of being afflicted with a condition or disease. Thus, the terms "subject" and "patient" are used interchangeably herein. The term "subject" also refers to an organism, tissue, cell, or collection of cells from a subject.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The synthetic descriptions and specific examples that follow are only intended for the purposes of illustration and are not to be construed as limiting in any manner to make compounds of the disclosure by other methods.

Example 1

Biomimetic Tolerogenic Artificial Antigen Presenting Cells for Regulatory T-Cell Induction 1.1 Overview Regulatory T cell (Treg)-based therapeutics are receiving increased attention for their potential to treat autoimmune disease and prevent transplant rejection. Adoptively transferred Tregs have shown promise in early clinical trials, but cell-based therapies are expensive and complex to implement, and "off-the-shelf" alternatives are needed. The presently disclosed subject matter investigates, in part, the potential of artificial antigen presenting cells (aAPCs) synthesized from a novel blend of PLGA and PBAE to convert naïve T cells to Tregs both in vitro and in vivo. The addition of PBAE to the aAPC core increased the conjugation efficiency of signal proteins to the particle surface and resulted in enhanced ability to bind to naïve T cells and induce Tregs with potent suppressive function. Furthermore, PLGA/PBAE tolerogenic aAPCs (T-aAPCs) supported the loading and sustained release of signal 3 cytokine TGF-β. A single dose of T-aAPCs administered intravenously to Black 6 mice resulted in an increased percentage of FOXP3+ within the CD4+ T cell population. PLGA/PBAE T-aAPC-induced FOXP3+ cells also demonstrated higher levels of FOXP3 expression. Thus, PLGA/PBAE T-aAPCs show potential as an "off-the-shelf" tolerance-induction therapy.

1.2 Introduction

Interest in regulatory T cells (Tregs) for antigen-specific immunotherapy stems from the discovery that a CD4+ CD25+ subset of T cells had the ability to suppress other cell types in response to self and non-self antigens. Sakaguchi et al., 1995. As primary mediators of peripheral tolerance, Tregs work to regulate the immune system through several mechanisms targeting effector T cells and APCs. They are capable of directly destroying effector cells via cytolysis and suppressing effector cells through release of inhibitory cytokines, including TGF-β, IL-10, and IL-35, or metabolic disruption via IL-2 starvation, transfer of cyclic adenosine monophosphate (cAMP), and adenosine release. Gliwinski, et al., 2017; Vignali et al., 2008. Tregs also can inhibit dendritic cell maturation and induce dendritic cells to release indoleamine 2,3-dioxygenase (IDO) to suppress effector T cells. Because of their ability to induce tolerance through a variety of mechanisms, a growing number of therapies are being designed to target Tregs to establish tolerance toward specific antigens or allogens of interest. Strategies include expansion of Tregs, or de novo induction of Tregs from naïve T cells.

Although adoptive transfer of Tregs has been shown to effectively treat and reverse disease models of diabetes, graft-versus-host-disease (GvHD), and experimental autoimmune encephalitis (EAE) and shows promise in early-phase clinical trials for GvHD, transplant, and autoimmune disease, the rarity of Tregs in peripheral blood presents a major challenge to obtaining enough cells for transfer. Gliwinski et al., 2017. In vitro expansions rely on high doses of IL-2 and have used APCs or anti-CD3/anti-CD28 beads. Tang et al., 2004; Yamazaki et al., 2003; and Sarkar et al., 2014. Tregs, however, are difficult to expand and may only be transiently functional following adoptive transfer. In vivo, Tregs have been expanded polyclonally using an IL-2/anti IL-2 monoclonal antibody (mAb) complex, Webster et al., 2009, although it has been shown that Ag-specific Tregs are more effective against disease than polyclonal Tregs. Tang et al., 2004. To expand Ag-specific Tregs in vivo, soluble MHC peptide complexes have been administered on their own or in combination with an IL-2/anti-IL-2 mAb complex. Li et al., 2009; Lin et al., 2010. In vivo Treg expansion may be hampered by absent or impaired existing Tregs. Low Treg numbers or defective function have been shown to contribute to a variety of autoimmune diseases, including type 1 diabetes (T1D), multiple sclerosis (MS), and systemic lupus erythematosus (SLE). Long and Buckner, 2011.

In cases where preexisting Tregs are nonexistent or impaired, Treg induction has the potential to restore numbers and function and may be a more promising strategy than expansion of existing Tregs. There is a lack of effective technologies for antigen-specific Treg induction, however, particularly those that can be used to induce Tregs in vivo. Naïve T cells can be converted to Tregs through co-stimulation and TGF-β, the latter essential for transition to a regulatory phenotype. Long and Buckner, 2011; Chen et al., 2003. McHugh et al. showed that local TGF-β and IL-2 release in a controlled paracrine fashion from nanoparticles generated induced Tregs (iTregs) from naïve CD4+ T cells that were both functional and stable over time. McHugh et al., 2015. Controlled cytokine release to modulate T-cell responses has also been explored in the context of aAPC design. Signal 3 cytokines released from PLGA-based aAPCs have been shown to enhance the ability of aAPCs to expand Ag-specific T cells and inhibit tumor growth in a mouse model, Zhang et al., 2017, as well as allowing polarization of the T-cell repertoire. McHugh et al, 2015; Steenblock et al., 2011. aAPCs have been used extensively to activate T cells, but not to induce regulatory T cells to promote immune tolerance.

One promising area of research is the use of different biodegradable polymers for the plastic core of aAPCs to increase their potency and "off-the-shelf" potential. Although poly(lactic-co-glycolic acid) (PLGA) is most commonly used, other biodegradable materials may possess beneficial properties for the construction of aAPCs. One important parameter governing T-cell activation is the surface density of signal proteins. Sunshine et al., 2014. Close spacing is optimal but can be difficult to achieve with PLGA particles due to the low efficiency of certain conjugation strategies. To generate enhanced aAPCs, the presently disclosed subject matter utilizes a novel core material consisting of a blend of PLGA and a hydrophobic poly(beta-amino ester) (PBAE). Rigid particles composed of a PLGA/PBAE blend have previously been used for intracellular nucleic acid delivery to immune cells. Little et al., 2004. Incorporating a hydrophobic, cationic polymer into the core of aAPCs has the potential to increase protein binding to the surface of the particles. Champion and Mitragotri, 2006. The addition of PBAE may enhance aAPC function and make it sufficiently potent for direct in vivo administration.

The presently disclosed subject matter investigates the ability of a biomimetic, biodegradable tolerogenic aAPC (T-aAPC) composed of a PLGA/PBAE blend to induce Tregs in vitro and in vivo to promote immune tolerance. PLGA/PBAE T-aAPCs improved Treg induction in vitro and in vivo over PLGA T-aAPCs, showing the importance of biomaterial chemistry is aAPC design. Induced Tregs were able to suppress the proliferation of naïve T cells. These results demonstrate the effectiveness of PLGA/PBAE based aAPC over PLGA aAPC for enhanced Treg induction in vitro and the potential of our new T-aAPC design to improve T-cell polarization toward a regulatory phenotype in vivo.

1.3 Materials and Methods 1.3.1 Poly(Beta-Amino Ester) Synthesis and Characterization Poly(beta-amino ester) (PBAE) was synthesized using a two-step procedure. First, an acrylate-terminated base polymer was prepared through the Michael addition of 4,4'-trimethylenedipiperidine (Sp) to 1,4-butanediol diacrylate (B4) at a 1.2:1 monomer ratio. The monomers were reacted neat and with stirring at 90° C. for 24 hours to generate the base polymer. Next, the base polymer was dissolved in anhydrous tetrahydrofuran (THF) and reacted with an excess of end-capping monomer 1-(3-aminopropyl)-4-methylpiperazine (E7) at room temperature for 1 hour. The resulting end-capped PBAE polymer was purified with hexane, dried under vacuum, and stored at −20° C. under nitrogen gas. The molecular weight of the PBAE was determined through gel permeation chromatography using an Ultrastyragel column with a molecular weight range of 500-30 kDa (Waters; Milford, MA) and a mobile phase of THF with 5% DMSO and 1% piperidine.

1.3.2 Tolerogenic Artificial Antigen Presenting Cell Synthesis and Characterization 1.3.2.1 Particle Fabrication Microparticles were made from poly(lactic-co-glycolic acid) (PLGA, acid-terminated, 50:50 lactide:glycolide ratio, MW 34,000-58,000 Da), purchased from Sigma Aldrich (St. Louis, MO), or a 75:25 w/w blend of PLGA and PBAE. To synthesize blank particles, 100 mg of polymer was dissolved in 5 mL dichloromethane (DCM) and homogenized into a 50-mL solution of 1% poly(vinyl alcohol) (PVA) by a T-25 digital ULTRA-TURRAX IKA tissue homogenizer at a speed of 5,000 rpm (IKA Works; Wilmington, NC). The resulting microparticle emulsion was then added to 100 mL of 0.5% PVA. To synthesize TGF-β-releasing particles, 50 mg of polymer was dissolved in 1 mL DCM. A 17.5 μL solution containing 2.5 μg recombinant mouse TGF-β and 1 mg bovine serum albumin (BSA) was added into the polymer solution and emulsified using a Misonix S-4000 probe sonicator operating at 12 W power 20% amplitude for 20 seconds (Qsonica; Newtown, CT). The resulting TGF-0/polymer emulsion was homogenized into 50 mL of 1% PVA 5,000 rpm, and the final emulsion was added into 100 mL of 0.5% PVA with stirring. The particles were allowed to harden for at least 4 hours. Particles were then washed three times in water with centrifugation at 3,000×g, frozen, and lyophilized for later use.

1.3.2.2 Functionalization

PLGA and PLGA/PBAE microparticles were functionalized with proteins of interest using EDC/NHS chemistry, which couples primary amines on proteins of interest to carboxylic acid-terminated PLGA. Lyophilized particles were resuspended in 0.1 M MES buffer at pH 6.0 at a concentration of 2 mg/mL. A 100-4 EDC/NHS solution consisting of 40 mg/mL EDC and 48 mg/mL NHS was added to each 2-mg batch of particles. Particles were activated at room temperature for 30 minutes. Following activation, particles were centrifuged at 5,000×g for 5 minutes and resuspended in PBS at 2 mg/mL. Anti-mouse CD3 (Biolegend; San Diego, CA) and anti-mouse CD28 (Bio X Cell; West Lebanon, NH) monoclonal antibodies were added at the following amounts, expressed as the mass of anti-CD3/anti-CD28 per mg of particles: 0.8 μg/1 μg (⅕x); 4 μg/5 ug (1×); and 20 μg/25 μg (5×). Particles were incubated with the protein overnight at 4° C. to synthesize T-aAPCs. The following day, particles were washed 3 times with PBS and used immediately.

1.3.2.3 Characterization

Microparticles were imaged and sized using scanning electron microscopy (SEM). Lyophilized particles were spread onto aluminum tacks mounted with double-sided carbon tape. Excess particles were removed from the tack with an air gun. Samples were sputter-coated with a 20-nm layer of gold/palladium and imaged on a LEO FESEM (Zeiss). Particle size was measured by image analysis in ImageJ.

To assess TGF-β release from PLGA and PLGA/PBAE microparticles, lyophilized particles were resuspended in PBS at 10 mg/mL and incubated at 37° C. Supernatants were collected at various timepoints by centrifuging samples at 5,000×g and were replaced with fresh PBS. TGF-β in the supernatant was measured using a sandwich ELISA (Biolegend).

To quantify the amount of protein on the surface of T-aAPCs, T-aAPCs were conjugated with ⅕x, 1×, or 5×AlexaFluor 488-labeled anti-CD3 and APC-labeled anti-CD28 using EDC/NHS chemistry as described above. After conjugation, T-aAPCs were washed three times with PBS, and fluorescence was evaluated using a BioTek Synergy 2 plate reader (Biotek; Winooski, VT). The mass of protein on the particle was calculated against a standard curve generated from known amounts of labeled protein to evaluate protein conjugation efficiency.

1.3.3 In Vitro T-aAPC/T-Cell Binding Assay

PLGA and PLGA/PBAE microparticles were synthesized as previously described except the initial DCM solution also included 10 μg of Vybrant DiD Cell-Labeling Solution (Thermo Fisher Scientific; Waltham, MA). Control PLGA and PLGA/PBAE T-aAPCs were surface-conjugated with an anti-human CD3 monoclonal antibody (Biolegend; San Diego, CA). Black 6 mice were sacrificed, and their spleens were dissected and homogenized though a cell strainer. CD4+CD25− cells were isolated using a CD4+ T-cell isolation kit (Miltenyi Biotec; Auburn, CA). During CD4+ T-cell isolation, 1 μL biotinylated anti-mouse CD25 monoclonal antibody (Biolegend) was added per $10^7$ cells prior to magnetic separation. Following isolation, cells were labeled with Vybrant Cell Tracker carboxyfluorescein succinyl ester (CFSE) (Life Technologies; Grand Island, NY) dye according to the manufacturer's protocol. Cells were incubated with T-aAPCs at a concentration of 0.05 or 0.01 mg T-aAPCs/50,000 cells for 1 hour at 37° C. Confocal micrographs were obtained using a Zeiss 710 LSM (Carl Zeiss Microscopy; Jena, Germany). T-aAPC/T-cell binding was assessed on an Accuri C6 Flow Cytometer (BD Biosciences; San Jose, CA). Cells also were analyzed using flow cytometry. To calculate the fraction of bound cells, the percentage and geometric mean fluorescence intensity (MFI) of CFSE and DiD double-positive events was normalized to blank particle samples.

1.3.4 In Vitro T-aAPC-Mediated Treg Induction

All mice were maintained according to the Johns Hopkins University Institutional Animal Care and Use Committee. Black 6 mice were sacrificed, and their spleens were dissected and homogenized though a cell strainer. CD4+CD25− cells were isolated using a CD4+ T-cell isolation kit. During CD4+ isolation, 1 μL biotinylated anti-mouse CD25 was added per $10^7$ cells prior to magnetic separation. Cells were incubated with T-aAPCs at 1, 0.1, 0.01, or 0.001 mg/mL in RPMI media supplemented with L-glutamine, non-essential amino acids, vitamin solution, sodium pyruvate, β-mercaptoethanol, 10% FBS, ciprofloxacin, and 50 ng/mL human IL-2. TGF-β was added at 5 ng/mL. After five days, cells were stained with CFSE according to the manufacturer's protocol. CFSE-labeled cells were then fixed, permeabilized, and stained for Forkhead Box Protein 3 (FOXP3) using a FOXP3 staining kit (Thermo Fisher Scientific). FOXP3 expression was assessed through flow cytometry analysis on an Accuri C6 Flow Cytometer.

1.3.5 In Vitro Induced-Treg Suppression Assay

The functionality of induced Tregs was verified through their ability to suppress the proliferation of naïve CD4+ T cells. Tregs were induced for five days with 0.1 mg/mL PLGA or PLGA/PBAE T-aAPCs. After five days, suppressor populations were harvested. The responder population consisted of CD4+CD25− T cells isolated from Thy1.1 B6 mice and labeled with CFSE as previously described. Suppressor and responder populations were mixed at 1:1, 1:2, 1:4, 1:8 or 0:1 ratios in a 96-well plate (50,000 responder cells per well). Anti-CD3/anti-CD28 Dynabeads were added to each well at a 1:2 bead/responder cell ratio. After 3 days, cells were stained for Thy1.1 and analyzed using flow cytometry. Proliferation of responder cells was assessed through CFSE dilution. Since the CFSE dye is diluted in half with each cell division, each generation of cells is defined by a distinct peak on the CFSE histogram.

1.3.6 In Vivo T-aAPC-Mediated Treg Induction

The effectiveness of TGF-β-loaded T-aAPCs at polarizing CD4+ T cells toward a regulatory phenotype in vivo was investigated. TGF-β-releasing T-aAPCs were injected intravenously into B6 mice. Control mice received either TGF-β-releasing PLGA/PBAE particles or no treatment. After five days, mice were sacrificed and their spleens and lymph nodes were harvested. Single cell suspensions were generated through cell straining, and cells were stained for CD4 and FOXP3. Following staining, cells were analyzed using flow cytometry.

1.4. Results 1.4.1 T-aAPC Synthesis and Characterization

After synthesis via two sequential Michael addition reactions, Tzeng et al., 2011, the resulting PBAE had a number average molecular weight (Mn) of about 28 kDa and weight average molecular weight (Mw) of about 137 kDa. PLGA or PLGA/PBAE T-aAPCs were surface-functionalized with anti-CD3 as signal 1 and anti-CD28 for co-stimulation. PLGA and PLGA/PBAE T-aAPC size and morphology were evaluated using SEM. SEM images revealed that PLGA and PLGA/PBAE particles were spherical. Through image analysis, PLGA and PLGA/PBAE particles were determined to be similar in size, with an average diameter of about 3 μm (FIG. 8). This size enables T-aAPCs to approximate the biological length scale of the natural APC/T cell interaction while being small enough for systemic administration without pulmonary embolism.

T-aAPCs functionalized with anti-CD3 and anti-CD28 nonspecifically stimulate T cells, so TGF-β must be added exogenously or loaded into the particle core of the T-aAPCs to polarize CD4+ T cells toward a regulatory phenotype, and TGF-β release over time was quantified. PLGA and PLGA/PBAE particles degraded over the course of a month. Total TGF-β release from PLGA and PLGA/PBAE particles was 1.5 and 0.26 ng/mg particles, respectively (FIG. 5).

The surface protein content of PLGA and PLGA/PBAE T-aAPCs were compared across three different doses of anti-CD3 and anti-CD28 added into the conjugation media. Fluorescently labeled anti-CD3 and anti-CD28 were conjugated to the surface of particles, and the fluorescence intensity measurements were used to quantify the protein on the surface of newly synthesized T-aAPCs. PLGA/PBAE T-aAPCs were found to have significantly more bound anti-CD3 and anti-CD28 than PLGA T-aAPCs when ⅕, 1, or 5× protein doses were added to the conjugation media. Since PLGA/PBAE particles conjugate protein more efficiently than PLGA particles, less protein is needed to synthesize PLGA/PBAE T-aAPCs. 1.4.2 PLGA/PBAE T-aAPCs bind more frequently to naïve CD4+ T cells aAPC function is based on their ability to target and interact efficiently with T cells to present the necessary activation signals. T-cell activation is dependent on aAPC binding and signal presentation across the particle/cell interface. The ability of PLGA and PLGA/PBAE T-aAPCs to bind target cells were compared. A hydrophobic dye was encapsulated in the core of T-aAPCs during particle synthesis to generate fluorescent T-aAPCs. Fluorescent PLGA and PLGA/PBAE T-aAPCs were functionalized according to the previously described methods. Control T-aAPCs were surface-functionalized with anti-human CD3 antibody with no specific binding to the mouse TCR. PLGA and PLGA/PBAE T-aAPCs were incubated with CFSE-labeled CD4+CD25− T cells at 37° C. for one hour. Binding was visualized using confocal microscopy. Images show that PLGA/PBAE T-aAPCs bind to T cells more frequently than PLGA T-aAPCs, control T-aAPCs, and blank non-functionalized particles. The fraction of bound cells was determined by flow cytometry by gating on CFSE and DiD double-positive events, which indicate colocalization of T-aAPCs and T-cells. Background signal was determined from samples of blank PLGA and PLGA/PBAE particles and cells and was subtracted from calculated binding values. No significant binding of T-aAPCs with surface-bound anti-human CD3 was observed. The percentage of T cells bound to PLGA/PBAE T-aAPCs was 30%, compared to 7.7% bound to PLGA T-aAPC at the highest particle dose tested. The MFI of PLGA/PBAE T-aAPC binding events was 4.5-fold higher than that of PLGA T-aAPC binding events, indicating a higher average number of bound particles per T cell.

1.4.3 PLGA/PBAE T-aAPCs Induce More Tregs In Vitro

The potential of the presently disclosed PLGA and PLGA/PBAE T-aAPCs to induce Tregs from naïve CD4+ cells was tested in vitro. PLGA and PLGA/PBAE T-aAPCs with ⅕×, 1×, and 5× surface-bound signal protein densities were incubated with CD4+CD25− T cells for 5 days in the presence of TGF-β and IL-2 and then analyzed for Treg induction by flow cytometry. The surface protein density and T-aAPC dose was optimized for maximum conversion to the Treg phenotype and the ability of PLGA/PBAE and PLGA T-aAPC to induce Tregs was compared. A dose-dependent Treg induction was observed after incubation with T-aAPCs (FIG. 6). PLGA/PBAE T-aAPCs with all three tested surface protein densities outperformed PLGA T-aAPCs, generating significantly larger percentages of FOXP3+ cells at 1, 0.1, and 0.01 mg/mL T-aAPC doses. The greatest separation between PLGA and PLGA/PBAE T-aAPC performance occurred at a 0.1 mg/mL dose with T-aAPCs conjugated with 1× surface protein, so this protein density and T-aAPC dose was used for later experiments.

1.4.4 Induced Tregs Suppress Proliferation of CD4+ T Cells

The ability of induced Tregs to suppress T-cell proliferation was investigated to verify the suppressive potential of our T-aAPC. First, Treg induction was carried out over five days as previously described, using PLGA and PLGA/PBAE T-aAPCs at a 0.1 mg/mL dose. After the induction period, the suppressor populations were harvested, and FOXP3 levels were assessed (FIG. 7B). Suppressor populations were incubated at titrated doses with CFSE-labeled Thy1.1+ responder cells and anti-CD3/anti-CD28 Dynabeads for three days. On the third day, samples were analyzed using flow cytometry. Dose-dependent suppression of responder T cells was observed for T-aAPC-induced Tregs (FIG. 7C), with significantly less responder proliferation in the presence of PLGA/PBAE T-aAPC-induced suppressor populations than in the presence of PLGA T-aAPC-induced suppressor populations (FIG. 7D).

1.4.5 PLGA/PBAE T-aAPCs Increase Treg Levels In Vivo

The potential of T-aAPCs to polarize the endogenous T-cell repertoire toward a regulatory phenotype in vivo was evaluated. A 2-mg dose of TGF-β-loaded T-aAPCs or TGF-β-loaded unconjugated (blank) particles was administered intravenously to mice. Five days later, animals were sacrificed and T cells from the spleens and lymph nodes were stained for CD4 and FOXP3 expression. Cells were analyzed using flow cytometry, and FOXP3+ cells were quantified as a percentage of CD4+ cells. Administration of PLGA/PBAE T-aAPCs led to a 3% increase in FOXP3+ cells within the CD4+ population in the lymph nodes over control mice that did not receive particles. Significantly higher FOXP3 expression was observed in lymph node Tregs induced with PLGA/PBAE T-aAPCs than in those induced with PLGA T-aAPCs. Similar trends were observed in the spleen, although increases in the percentage of FOXP3+ cells and FOXP3 expression were not significant.

1.5 Discussion

Treg-based therapies are a promising approach to treat autoimmune disease and prevent transplant rejection, although a major barrier to their use is the lack of efficient expansion and induction techniques. Gliwinski et al., 2017. Particle-based systems represent a more "off-the-shelf" approach to establishing immune tolerance, which may be more easily translated. Recent advancements highlight the potential of biomimetic and biodegradable aAPCs as a clinical immunotherapy. They are typically used, however, in the context of adoptive transfer and have not been used to directly stimulate the endogenous T-cell repertoire or for Treg induction.

Here, a tolerogenic aAPC with a novel core material to induce Tregs from naïve T cells was developed and characterized. PLGA-based aAPCs have been shown to effectively stimulate T cells against tumor-specific antigens in adoptive transfer cancer models, and their strong biomimetic potential has been demonstrated through their ability to encapsulate and release signal 3 cytokines in a controlled and highly tunable manner. McHugh et al., 2015; Steenblock et al., 2011. PLGA was blended with an additional polymer, PBAE, to enhance aAPC potency. T-cell activation is dependent on surface protein spacing, with close spacing of signaling ligands being optimal. A density of 1000 anti-CD3 molecules/$\mu m^2$ has previously been shown to better activate CD4+ T cells compared to lower densities. Matic et al., 2013. The presently disclosed subject matter shows that the addition of PBAE to the aAPC core allowed protein conjugation to the particle surface at a higher density. The addition of PBAE, a hydrophobic polymer, may increase nonspecific adsorption of protein to the polymer surface, as it has been previously shown that protein can conjugate to the surface of hydrophobic polystyrene particles in the absence of other chemically active reagents. Champion and Mitragotri, 2006. Increased conjugation efficiency may allow PLGA/PBAE particles to achieve a more optimal surface protein density than PLGA particles.

Incorporation of PBAE in the aAPC core also enhanced aAPC binding to naïve CD4+ T cells, another critical aspect determining aAPC efficacy. Cheung et al., 2018. PLGA/PBAE T-aAPCs bound a higher percentage of CD4+ T cells than PLGA T-aAPCs and control T-aAPCs displaying an anti-human CD3 antibody. More frequent binding events for PLGA/PBAE may be attributed to the increased signal protein density on PLGA/PBAE aAPCs, since higher densities correlate to increased binding to T cells. Cheung et al., 2018. Although outside the scope of the current study, the addition of PBAE may also favorably alter the material properties of the aAPC core for enhanced interactions with T cells. For example, it has been shown that the elastic modulus of a polymeric substrate for T-cell activation can have a significant effect on T-cell activation and subsequent phenotype. O'Connor et al., 2012. In addition, lateral rigidity of the surface proteins has been shown to impact the magnitude and direction of an artificially directed T-cell response. Hsu et al., 2012. In both cases, softer, more pliable materials have been found to be more beneficial than PLGA.

PLGA/PBAE T-aAPCs were further able to robustly induce Tregs from naïve CD4+ splenocytes in vitro, outperforming PLGA T-aAPCs and soluble factors over a range of surface-bound signal protein densities tested. These effects are likely due in part to increased surface protein on PLGA/PBAE T-aAPCs. Induction levels were highest when a 1× protein dose (4 μg anti-CD3 and 5 μg anti-CD28 per mg particles) was conjugated to PLGA/PBAE particles during aAPC synthesis, compared to a 5× or ⅕× dose (FIG. 6). Meanwhile, low levels of induction were observed for PLGA T-aAPCs, and the best performance was observed at a 5× protein dose. Increased protein density correlates with improved Treg induction potential. For PLGA/PBAE T-aAPCs, a high protein dose during conjugation (20 μg anti-CD3 and 25 μg anti-CD28 per mg particles) may be too immunostimulatory, thereby decreasing the efficiency of Treg induction. In addition to altering the overall surface protein density, robust stimulatory capacity of PLGA/PBAE T-aAPC can potentially be modulated by increasing the ratio of signal 1 to signal 2 proteins to favor Treg formation. Importantly, T-aAPC-induced suppressor populations were able to suppress the proliferation of naïve CD4+ T cells in vitro in a dose-dependent manner (FIG. 7). Excitingly, the PLGA/PBAE T-aAPC-induced suppressor population almost completely suppressed the proliferation of responder cells, while populations induced by PLGA T-aAPCs, a combination of plate-bound and soluble signal proteins, or soluble cytokines demonstrated less potent suppressive activity.

Finally, the effectiveness of PLGA/PBAE T-aAPCs at inducing Tregs directly in vivo was studied. Since TGF-β is necessary for the development of the Treg phenotype, it was desired to encapsulate it within our T-aAPCs to achieve sustained, local release. Local release of TGF-β has previously been shown to mediate more effective Treg conversion than equivalent soluble concentrations. McHugh et al., 2015. T-aAPCs loaded with TGF-β were synthesized and their sustained release from PLGA and PLGA/PBAE T-aAPCs was demonstrated (FIG. 5). A single dose of PLGA/PBAE T-aAPCs administered intravenously was sufficient to significantly bias the T-cell repertoire in the lymph nodes toward a regulatory phenotype in vivo compared mice receiving no treatment (FIG. 8). The same trend was observed in the spleen, although the results were not statistically significant at an α-level of 0.05. PLGA T-aAPCs were unable to significantly bias the repertoire towards Tregs despite their ability to release more TGF-β than PLGA/PBAE T-aAPCs. Overall, the presently disclosed data suggest that PLGA/PBAE has the potential to be used in vivo for polyclonal Treg induction.

These results demonstrate that the addition of PBAE to the aAPC core confers superior properties to the aAPC, including increased surface protein density, enhanced binding to naïve T cells, and more efficient T-cell activation and polarization, as illustrated by their ability to more effectively induce conversion of naïve T cells to Tregs. The PLGA/PBAE T-aAPC platform's enhanced potency, suitability in vivo, and versatility give it potential as an "off-the-shelf" tolerance induction therapy. PLGA/PBAE may also be a promising core material for aAPCs to activate the immune system, such as for cancer immunotherapy.

1.6 Summary

Here, a biomimetic polymeric artificial antigen presenting cell capable of polarizing T cells toward a regulatory lineage has been developed. The addition of PBAE to the core material of PLGA-based aAPCs increases protein conjugation efficiency to particulate cores and enhances the ability of aAPCs to interact with T cells and convert them to functional Tregs in vitro. These biodegradable T-aAPCs support the sustained release of signal 3 cytokine TGF-β. TGF-β-loaded PLGA/PBAE T-aAPCs were further shown to increase the frequency of Tregs in vivo following a single intravenous injection. PLGA/PBAE may be a promising material for the construction of aAPC with potent immunomodulatory capacity and potential application for clinical tolerance induction therapy.

Example 2

This example demonstrates antigen-specific engagement of T cells by peptide/MHC-coated MPs.

MPs of approximately 1 μm diameter were fabricated from poly(lactic-co-glycolic acid) (PLGA) or a 75:25 (w/w) blend of PLGA to poly(beta-amino ester) (PBAE). EDC/NHS chemistry was used to conjugate I-Ab OVA(329-337)-loaded MHC II tetramer to the surface of the particles to generate ova-MPs. A control I-A(b) tetramer was used to generate control MPs. $CD4^+$ T cells were enriched from OT-II mice, labelled with CFSE, and incubated with 0.01 mg fluorescent MPs for 1 hour at 37° C. to evaluate the extent of OVA-specific binding using flow cytometry. Compared to blank particle controls, OVA peptide-loaded MHC-coated MPs demonstrated enhanced engagement of OVA-specific $CD4^+$ T cells, illustrating that coated MPs can achieve antigen-specific T cell engagement (FIG. 15).

Example 3

This example describes the generation of TolAPCs that effect antigen-specific $T_{Reg}$ induction.

OVA peptide/MHC tetramer-coated and control TolAPCs were synthesized as in Example 2, except that during conjugation, a monoclonal antibody directed against CD28 was also added as a costimulatory signal. Naïve $CD4^+$ T cells were harvested from OT-II mice and incubated with TolAPCs for 3 days in the presence of IL-2 and TGF-β. Following incubation, cells were stained for FOXP3 to assess $T_{Reg}$ cell induction. TolAPCs surface-conjugated with OVA peptide/MHC tetramers and anti-CD28 induced OVA-specific $T_{Reg}$ cells from naïve OT-II CD4+ T cells, whereas TolAPC surface-conjugated with control tetramer did not induce $T_{Reg}$ cells, as shown in FIG. 26. These data indicate that TolAPCs can induce $T_{Reg}$ cells in an antigen-specific manner.

Nano-scale TolAPCs with surface-conjugated proteins also were generated. Specifically, PLGA or PLGA/PBAE nanoparticles (approximately 200 nm in diameter) were synthesized using emulsion techniques. Four proteins were chemically coupled to the surface of TolAPCs to provide specificity and regulatory cues for $T_{Reg}$ cell induction: (i) OVA peptide/MHC tetramers, (ii) a monoclonal antibody against CD28, (iii) TGF-0, and (iv) IL-2. TolAPCs were cultured with primary naïve $CD4^+$ T cells isolated from OT-II mice. Flow cytometry was used to assess TolAPC/T cell binding and $T_{Reg}$ cell induction based on FOXP3 staining. Nanoscale TolAPCs induced up to 45% ovalbumin-specific $T_{Reg}$ cells without the presence of any exogenous factors (FIG. 17), further supporting the use of TolAPCs for antigen-specific $T_{Reg}$ cell induction.

Anisotropic nano-TolAPCs with surface-conjugated signals also were prepared. PLGA or PLGA/PBAE nanoparticles (approximately 200 nm in diameter) were synthesized using emulsion techniques. Using an automated thin-film stretching device, spherical particles were mechanically stretched along one axis to an aspect ratio of 2:1 to generate ellipsoidal particles. Four proteins were chemically coupled to the surface of spherical or ellipsoidal TolAPCs to provide specificity and regulatory cues for $T_{Reg}$ cell induction: (i) OVA peptide/MHC tetramers, (ii) a monoclonal antibody against CD28, (iii) TGF-β, and (iv) IL-2. TolAPCs were cultured with primary naïve $CD4^+$ T cells isolated from OT-II mice. Flow cytometry was used to assess TolAPC/T cell binding and $T_{Reg}$ cell induction via FOXP3 staining. Ellipsoidal nano-TolAPCs improved $T_{Reg}$ cell induction compared to spherical nano-TolAPCs, as shown in FIG. 18.

Example 4

This example describes the generation of TolAPCs comprising a protein or small molecule encapsulated within the particle core.

PLGA microparticles loaded with varying amounts of the TGF-β cytokine and the small molecule immunosuppressive drug rapamycin were synthesized using a double emulsion technique. Rapamycin loading efficiency was determined by UV spectrophotometry and TGF-β release was measured by ELISA. Particles were surface-functionalized with ova peptide-loaded I-A(b) MHC II tetramers and anti-CD28 to generate TolAPCs. Naïve $CD4^+$ T cells isolated from OT-II mice were incubated with TolAPCs for 3 days in the presence of IL-2. Cells were then analyzed for FOXP3 levels via flow cytometry. TolAPCs containing TGF-β and rapamycin elicited robust $T_{Reg}$ cell induction, and loading doses of 125 ng TGF-β and 25 μg rapamycin/mg PLGA during TolAPC synthesis were found to be most effective (FIG. 19).

REFERENCES

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art.

Sakaguchi, S., Sakaguchi, N., Asano, M., Itoh, M. & Toda, M. Immunologic self-tolerance maintained by activated T cells expressing IL-2 receptor alpha-chains (CD25). Breakdown of a single mechanism of self-tolerance causes various autoimmune diseases. *J Immunol* 155, 1151-1164 (1995).

Gliwinski, M., Iwaszkiewicz-Grzes, D. & Trzonkowski, P. Cell-Based Therapies with T Regulatory Cells. *BioDrugs* 31, 335-347 (2017).

Vignali, D. A., Collison, L. W. & Workman, C. J. How regulatory T cells work. *Nat Rev Immunol* 8, 523-532 (2008).

Tang, Q., et al. In vitro-expanded antigen-specific regulatory T cells suppress autoimmune diabetes. *J Exp Med* 199, 1455-1465 (2004).

Yamazaki, S., et al. Direct expansion of functional CD25+ CD4+ regulatory T cells by antigen-processing dendritic cells. *J Exp Med* 198, 235-247 (2003).

Sarkar, D., et al. Ex Vivo Expanded Autologous Polyclonal Regulatory T Cells Suppress Inhibitor Formation in Hemophilia. *Mol Ther Methods Clin Dev* 1(2014).

Webster, K. E., et al. In vivo expansion of T reg cells with IL-2-mAb complexes: induction of resistance to EAE and long-term acceptance of islet allografts without immunosuppression. *J Exp Med* 206, 751-760 (2009).

Li, L., Yi, Z., Wang, B. & Tisch, R. Suppression of ongoing T cell-mediated autoimmunity by peptide-MHC class II dimer vaccination. *J Immunol* 183, 4809-4816 (2009).

Lin, M., et al. Reversal of type 1 diabetes by a new MHC II-peptide chimera: "Single-epitope-mediated suppression" to stabilize a polyclonal autoimmune T-cell process. *Eur J Immunol* 40, 2277-2288 (2010).

Long, S. A. & Buckner, J. H. CD4+FOXP3+T regulatory cells in human autoimmunity: more than a numbers game. *J Immunol* 187, 2061-2066 (2011).

Chen, W., et al. Conversion of peripheral CD4+CD25− naïve T cells to CD4+CD25+ regulatory T cells by TGF-beta induction of transcription factor Foxp3. *J Exp Med* 198, 1875-1886 (2003).

McHugh, M. D., et al. Paracrine co-delivery of TGF-beta and IL-2 using CD4-targeted nanoparticles for induction and maintenance of regulatory T cells. *Biomaterials* 59, 172-181 (2015).

Zhang, L., et al. Paracrine release of IL-2 and anti-CTLA-4 enhances the ability of artificial polymer antigen-presenting cells to expand antigen-specific T cells and inhibit tumor growth in a mouse model. *Cancer Immunology, Immunotherapy* 66, 1229-1241 (2017).

Steenblock, E. R., Fadel, T., Labowsky, M., Pober, J. S. & Fahmy, T. M. An artificial antigen-presenting cell with paracrine delivery of IL-2 impacts the magnitude and direction of the T cell response. *The Journal of Biological Chemistry* 286, 34883-34892 (2011).

Sunshine, J. C., Perica, K., Schneck, J. P. & Green, J. J. Particle shape dependence of CD8+ T cell activation by artificial antigen presenting cells. *Biomaterials* 35, 269-277 (2014).

Little, S. R., et al. Poly-beta amino ester-containing microparticles enhance the activity of nonviral genetic vaccines. *Proc Natl Acad Sci USA* 101, 9534-9539 (2004).

Champion, J. A. & Mitragotri, S. Role of target geometry in phagocytosis. *Proc Natl Acad Sci USA* 103, 4930-4934 (2006).

Tzeng, S. Y., et al. Non-viral gene delivery nanoparticles based on poly(beta-amino esters) for treatment of glioblastoma. *Biomaterials* 32, 5402-5410 (2011).

Matic, J., Deeg, J., Scheffold, A., Goldstein, I. & Spatz, J. P. Fine tuning and efficient T cell activation with stimulatory aCD3 nanoarrays. *Nano Lett* 13, 5090-5097 (2013).

Cheung, A. S., Zhang, D. K. Y., Koshy, S. T. & Mooney, D. J. Scaffolds that mimic antigen-presenting cells enable ex vivo expansion of primary T cells. Nat *Biotechnol* 36, 160-169 (2018).

O'Connor, R. S., et al. Substrate rigidity regulates human T cell activation and proliferation. *J Immunol* 189, 1330-1339 (2012).

Hsu, C. J., et al. Ligand mobility modulates immunological synapse formation and T cell activation. *PLoS One* 7, e32398 (2012).

Although the foregoing subject matter has been described in some detail by way of illustration and example for purposes of clarity of understanding, it will be understood by those skilled in the art that certain changes and modifications can be practiced within the scope of the appended claims.

That which is claimed:

1. A biodegradable particle comprising a blend of a polyester and a poly(beta-amino ester) (PBAE) with at least one soluble protein or small molecule encapsulated within the particle and at least two types of protein attached to a surface of the particle or to a coating on the surface thereof, wherein the at least two types of protein attached to a surface of the particle or to a coating on the surface thereof include a "Signal 1" protein that binds to an immune cell and a "Signal 2" protein that acts as a co-stimulatory molecule to immune cells, and wherein the Signal 1 protein and the Signal 2 protein have a ratio of Signal 1 protein to Signal 2 protein selected from about 1:1, 1.5:1, 2:1, 5:1, and 10:1.

2. The biodegradable particle of claim 1, wherein the polyester is selected from the group consisting of poly (lactic-co-glycolic acid) (PLGA), polycaprolactone (PCL), polyglycolide (PGA), poly(lactic acid) (PLA), a polyhydroxyalkanoate (PHA), poly-3-hydroxybutyrate (P3HB), poly(3-hydroxybutyrate-co-3-hydroxyvalerate) (PHBV), and combinations or blends thereof.

3. The biodegradable particle of claim 1, wherein the immune cell to which the Signal 1 protein binds comprises a T cell.

4. The biodegradable particle of claim 1, wherein the Signal 1 protein is selected from the group consisting of an anti-CD3 monoclonal antibody, major histocompatibility complex (MHC)-peptide complex (including human leukocyte antigen (HLA) complex), and one or more T-cell receptor (TCR) binders.

5. The biodegradable particle of claim 1, wherein the Signal 2 protein is selected from the group consisting of anti-CD28, 4-1BBL, CD80, CD86, and OX40L.

6. The biodegradable particle of claim 1, wherein the at least one soluble protein encapsulated within the particle comprises a “Signal 3” protein.

7. The biodegradable particle of claim 6, wherein the “Signal 3” protein is an interleukin and/or a cytokine.

8. The biodegradable particle of claim 7, wherein the cytokine comprises transforming growth factor beta 1 (TGF-β1).

9. The biodegradable particle of claim 1, wherein the small molecule comprises rapamycin or an analog thereof.

10. The biodegradable particle of claim 1, wherein the particle is a microparticle having an average diameter of from about 1 micron to about 5 microns.

11. The biodegradable particle of claim 1, wherein the particle is a nanoparticle having an average diameter of from about 50 nm to about 1000 nm.

12. The biodegradable particle of claim 1, wherein the particle is anisotropic and has a non-spherical shape.

13. The biodegradable particle of claim 1, wherein the particle has a prolate ellipsoidal shape.

14. The biodegradable particle of claim 1, wherein the particle has a coating comprising one or more synthetic and/or natural lipids and/or lipid membranes.

15. The biodegradable particle of claim 14, wherein the at least two types of protein are attached to the coating, which comprises one or more synthetic and/or natural lipids and/or lipid membranes.

16. The biodegradable particle of claim 1, wherein the Signal 1 protein and the Signal 2 protein are present on the particle in a 5:1 molar ratio.

17. A method for treating a disease or condition in subject in need of treatment thereof, the method comprising administering to the subject a therapeutically effective amount of a biodegradable particle of claim 1.

18. The method of claim 17, wherein the disease or condition comprises an auto-immune disease.

19. The method of claim 17, wherein the disease or condition comprises type 1 diabetes.

20. The method of claim 17, wherein the condition includes treating a subject pre-transplantation or post-transplantation.

21. A method for modulating an immune response in a subject, the method comprising administering an effective amount of a biodegradable particle of claim 1.

22. The method of claim 21, wherein the subject is afflicted with an autoimmune disease.

23. A kit containing the biodegradable particle of claim 1.

* * * * *